United States Patent [19]
Gapud et al.

[11] Patent Number: 5,981,511
[45] Date of Patent: *Nov. 9, 1999

[54] HYDROXYAMIDINO DERIVATIVES USEFUL AS NITRIC OXIDE SYNTHASE INHIBITORS

[75] Inventors: Rolando E. Gapud, Chicago; Timothy J. Hagen, Gurnee; Ann E. Hallinan, Evanston; Donald W. Hansen, Jr., Skokie, all of Ill.; Robert E. Manning, St. Louis; Suzanne Metz, Chesterfield, both of Mo.; Barnett S. Pitzele, Skokie, Ill.; Foe S. Tjoeng, Manchester, Mo.; Mihaly V. Toth, St. Louis, Mo.; R. Keith Webber, St. Peters, Mo.

[73] Assignee: G.D. Searle & Co., Chicago, Ill.

[*] Notice: This patent is subject to a terminal disclaimer.

[21] Appl. No.: 08/813,545

[22] Filed: Mar. 5, 1997

Related U.S. Application Data

[63] Continuation-in-part of application No. 08/689,463, Aug. 8, 1996
[60] Provisional application No. 60/012,904, Mar. 6, 1996.

[51] Int. Cl.⁶ ............... C07F 7/08; A01N 55/00
[52] U.S. Cl. ............... 514/63; 514/24; 514/378; 514/386; 514/389; 514/398; 514/467; 514/561; 514/562; 514/529; 514/546; 514/551; 514/256; 548/240; 548/245; 548/349.1; 540/485; 540/487; 540/528; 549/215; 549/451; 549/452; 556/418; 556/419; 556/420; 556/422; 562/26; 562/27; 562/433; 562/440; 562/899; 560/147; 560/153; 560/156; 560/168; 564/225; 564/229
[58] Field of Search .................. 548/240, 245, 548/349.1; 540/485, 487, 528; 549/215, 451, 452; 556/418, 419, 420, 422; 562/26, 27, 433, 440, 899; 560/147, 153, 156, 168; 569/225, 229; 514/63, 211, 378, 386, 389, 398, 467, 561, 562, 529, 546, 551, 256

[56] References Cited

U.S. PATENT DOCUMENTS

| | | |
|---|---|---|
| 4,713,369 | 12/1987 | Stüber . |
| 5,059,712 | 10/1991 | Griffith . |
| 5,081,148 | 1/1992 | Braquet et al. . |
| 5,132,453 | 7/1992 | Griffith . |
| 5,196,450 | 3/1993 | Sjoerdsma et al. . |
| 5,273,875 | 12/1993 | Griffith . |
| 5,281,627 | 1/1994 | Griffith . |
| 5,362,744 | 11/1994 | Purchase, Jr. et al. . |
| 5,364,881 | 11/1994 | Griffith et al. . |
| 5,464,858 | 11/1995 | Griffith et al. . |
| 5,684,008 | 11/1997 | Hallinan et al. ............ 514/256 |

FOREIGN PATENT DOCUMENTS

| | | |
|---|---|---|
| 0370320 | 5/1990 | European Pat. Off. . |
| 0446699 | 9/1991 | European Pat. Off. . |
| 2240041 | 7/1991 | United Kingdom . |
| 91/04023 | 4/1991 | WIPO . |
| 91/04024 | 4/1991 | WIPO . |
| 93/13055 | 7/1993 | WIPO . |
| 93/16721 | 9/1993 | WIPO . |
| 93/24126 | 12/1993 | WIPO . |
| 94/14780 | 7/1994 | WIPO . |
| 95/00505 | 1/1995 | WIPO . |
| 95/11014 | 4/1995 | WIPO . |
| 95/24382 | 9/1995 | WIPO . |
| 95/25717 | 9/1995 | WIPO . |
| 96/06076 | 2/1996 | WIPO . |
| 96/15120 | 5/1996 | WIPO . |

OTHER PUBLICATIONS

Gould et al., "Nucleoside Intermediates in Blasticidin S Biosynthesis Identified by the In Vivo Use of Enzyme Inhibitors", Can. J. Chem., vol. 72, pp. 6–11, 1994.

Tsunematsu et al., "β–Naphthylamides of Guanidinophenyl Amino Acids as Substrates of Aminopeptidases", Chem. Pharm. Bull., vol. 36, No. 3, pp. 1205–1209, 1988.

Funabashi et al., "A New Anti–MRSA Dipeptide, TAN–1057 A", Tetrahedron, vol. 49, No. 1, pp. 13–28, 1993.

Prabhakaran et al., "Studies on Nitrogen Metabolism Using $^{13}$C NMR Spectroscopy. 5.$^1$ Metabolism of L–α–Arginine in the Biosynthesis of Blasticidin S", Tetrahedron, vol. 27, No. 33, pp. 3815–3818, 1986.

Stuehr et al., "Mammalian Nitric Oxide Synthases", Advances in Enzymology, vol. 65, 1992, (p. 317).

Plapp et al., "Determination of δ–Acetimidyllysine in Proteins" Analytical Biochemistry, vol. 62, pp. 291–294, 1974.

Rees et al., "Characterization of Three Inhibitors of Endothelial Nitric Oxide Synthase in vitro and in vivo", Br. J. Pharmacol., vol. 101, pp. 746–752, 1990.

Proudfoot et al., "Conformation–directed Recombination of Enzyme–activated Peptide Fragments: A Simple and Efficient Means to Protein Engineering", J. Bio. Chem., vol. 264, No. 15, pp. 8764–8770, 1989.

Palacios, et al., "Nitric Oxide from L–Arginine Stimulates the Soluble Guanylate Cyclase in Adrenal Glands", Biochemical and Biophysical Research Communications, vol. 165, No. 2, pp. 802–809, 1989.

Knowles et al., "Kinetic Characteristics of Nitric Oxide Synthase from Rat Brain", Biochem. J., vol. 269, pp. 207–210, 1990.

CA 107, 40336y, 1987.
CA 63, 5641d, 1965.
CA 97, 38442m, 1982.
CA 76, 43768t, 1972.
CA 118, 72838g, 1993.
CA 64, 17593h, 1966.
CA 115, 29868t, 1991.
CA 104, 202858, 1986.

Primary Examiner—Paul F. Shaver
Attorney, Agent, or Firm—Alan L. Scrivner

[57] ABSTRACT

The current invention discloses hydroxyamidino derivatives useful as nitric oxide synthase inhibitors.

10 Claims, No Drawings

HYDROXYAMIDINO DERIVATIVES USEFUL AS NITRIC OXIDE SYNTHASE INHIBITORS

BACKGROUND OF THE INVENTION

1. Field of the Invention

The present invention relates to hydroxyamidino derivatives and their use in therapy, in particular their use as nitric oxide synthase inhibitors and is a continuation-in-part of U.S. patent application Ser. No. 08/689,463 filed Aug. 8, 1996 filed originally as a provisional application serial no. 60/012,904 on Mar. 6, 1996.

2. Related Art

It has been known since the early 1980's that the vascular relaxation brought about by acetylcholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amyl nitrite, glyceryltrinitrate and other nitrovasodilators. The recent identification of EDRF as NO has coincided with the discovery of a biochemical pathway by which NO is synthesized from the amino acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacology*, 38, 1709–1715 (1989) and Moncada et al, *Pharmacological Reviews*, 43, 109–142 (1991). It is now thought that excess NO production may be involved in a number of conditions, particularly conditions which involve systemic hypotension such as toxic shock and therapy with certain cytokines.

The synthesis of NO from L-arginine can be inhibited by the L-arginine analog, L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed this inducible NO synthase synthesizes NO for long periods.

The NO released by the constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely from the effects of NO synthesized by the inducible NO synthase.

There is also a growing body of evidence that NO may be involved in the degeneration of cartilage which takes place in certain conditions such as arthritis and it is also known that NO synthesis is increased in rheumatoid arthritis. Accordingly, further conditions in which there is an advantage in inhibiting NO production from L-arginine include auto immune and/or inflammatory conditions affecting the joints, for example arthritis, inflammatory bowel disease, cardiovascular ischemia, diabetes, congestive heart failure, myocarditis, atherosclerosis, migraine, reflux esophagitis, diarrhea, irritable bowel syndrome, cystic fibrosis, emphysema, hyperalgesia (allodynia), cerebral ischemia (both focal ischemia, thrombotic stroke and global ischemia, secondary to cardiac arrest), other central nervous system disorders mediated by NO and other disorders mediated by NO including opiate tolerance in patients needing protracted opiate analgesics, and benzodiazepine tolerance in patients taking benzodiazepines, and other addictive behavior, for example, nicotine and eating disorders.

Further conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy.

Some of the NO synthase inhibitors proposed for therapeutic use so far, and in particular L-NMMA, are non-selective in that they inhibit both the constitutive and the inducible NO synthase. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use.

WO94/12165, WO94/14780, WO93/13055, EP0446699A1 and U.S. Pat. No. 5,132,453 disclose compounds that inhibit nitric oxide synthesis and preferentially inhibit the inducible isoform of nitric oxide synthase. The disclosures of which are hereby incorporated by reference in their entirety as if written herein.

SUMMARY OF THE INVENTION

In a broad aspect, the present invention is directed to inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering.

Compounds of the present invention are represented by the following chemical formula:

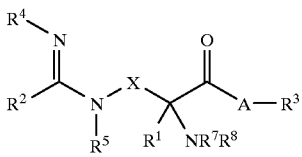

(I)

and pharmaceutically acceptable salts, wherein:

A is selected from O (oxygen) or S and may be taken together with $R^4$ to form a heterocyclic ring; or A is N when $R^3$ and $R^7$ are taken together to form a heterocyclic ring; or $R^5$ and A—$R^3$ are taken together to form a covalent bond; or A is N—$R^3$ provided $R^3$ is not a heterocyclic radical;

$R^1$ is not present or is selected from the group consisting of hydrogen, hydroxyalkyls, alkoxyalkyls, lower alkyls and haloalkyls;

$R^2$ is selected from the group consisting of straight and branched lower alkyls, lower alkenyls, and lower alkynyls, cycloalkyls, cycloalkenyls, haloalkyls;

$R^3$ is selected from the group consisting of aryl, heteroaryl, alkylaryl, alkylheteroaryl, all optionally substituted by one or more of halogen, nitrile, carboxy, carboxyalkyl, carboxyalkylaryl; or $R^3$ is selected from the group consisting of H, alkyl, alkenyl, $CH_2OC(=O)YR^6$, alkylhydroxy, alkylpolyhydroxy, alkyl (poly)oxyacyl, alkylcarboxy, optionally substituted by one or more of alkyl, hydroxy, amino, carboxy, carboxyalkyl, alkylcarbonyl;

$R^4$ is selected from H, OH, SH, $OR^6$, $SR^6$, $OC(=O)R^6$, $SC(=O)R^6$, $CH_2OC(=O)YR^6$, $OC(=O)YR^6$, $SC(=O)YR^6$;

Y is independently selected from O, S, $CH_2$, $CHR^6$, $C(R^6)_2$, NH, $NR^6$;

$R^5$ is selected from H, OH, SH, $OR^6$, $SR^6$, $OC(=O)R^6$, $SC(=O)R^6$, $CH_2OC(=O)YR^6$, $OC(=O)YR^6$, $SC(=O)YR^6$; provided that $R^4$ and $R^5$ are not simultaneously hydrogen or $CH_2OC(=O)YR^6$.

$R^6$ is selected from hydrogen, alkyl, alkenyl, alkynyl, cycloalkyl, heterocyclic, aryl, heteroaryl all optionally substituted by one or more alkyl, alkoxy, hydroxy, halogen, trifluoromethyl, nitro, cyano, or amino groups;

$R^7$ is selected from H, $S(O)R^9$, $SO_2R^9$, $CH_2OC(O)$—$R^9$, $C(O)$—$R^9$ where $C(O)$—$R^9$ can represent natural and synthetic amino acids or $R^9$ can be defined as below, or $R^7$ and $R^3$ taken together comprise a 5- or 6- membered heterocyclic ring containing two or more heteroatoms, optionally substituted with alkyl and/or oxygen functions including carbonyl, or taken together comprise a metal complex containing a divalent cation, or a boron complex;

$R^8$ is selected from H, acyl;

$R^9$ is selected from substituted dihydropyridyl, alkyl, thioalkoxy, alkoxy, amino, cycloalkoxy, optionally substituted with one or more of amino, alkyl, alkylaryl, heteroaryl, alkylheteroaryl, alkylmercaptoalkyl, which may optionally be substituted with one or more of hydroxy, amino, guanidino, iminoalkyl;

X is selected from the group consisting of lower alkylenes, lower alkenylenes and lower alkynylenes and which may optionally be substituted by one or more alkyl, alkoxy, hydroxy, halogen, trifluoromethyl, nitro, cyano, or amino groups; or X is selected from the group consisting of the formula —$(CH_2)_kQ(CH_2)_t$— where k is 1, 2 or 3, t is 1, 2 or 3 and Q is O (oxygen), Se, $SiE_2$ where E is lower alkyl, aryl, $S(O)_g$ where g is 0, 1 or 2, or NR where R is H or lower alkyl which may be optionally substituted with lower alkyl, lower alkoxy, hydroxy, halogen, trifluoromethyl, nitro, cyano, amino; or X is selected from the group consisting of the formula —$(CH_2)_mT(CH_2)_n$— where m is 0, 1 or 2, n is 0, 1 or 2, T is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

It is an object of the present invention to provide compounds that have usefulness as inhibitors of nitric oxide synthase. These compounds also preferentially inhibit the inducible form over the constitutive forms.

DETAILED DESCRIPTION OF THE INVENTION

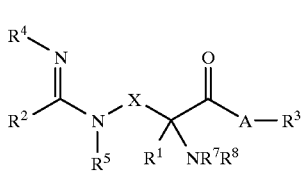

(I)

and pharmaceutically acceptable salts, wherein:

A is selected from O (oxygen) or S and may be taken together with $R^4$ to form a heterocyclic ring; or A is N when $R^3$ and $R^7$ are taken together to form a heterocyclic ring; or $R^5$ and A—$R^3$ are taken together to form a covalent bond; or A is N—$R^3$ provided $R^3$ is not a heterocyclic radical;

$R^1$ is not present or is selected from the group consisting of hydrogen, hydroxyalkyls, alkoxyalkyls, lower alkyls and haloalkyls;

$R^2$ is selected from the group consisting of straight and branched lower alkyls, lower alkenyls, and lower alkynyls, cycloalkyls, cycloalkenyls, haloalkyls;

$R^3$ is selected from the group consisting of aryl, heteroaryl, alkylaryl, alkylheteroaryl, all optionally substituted by one or more of halogen, nitrile, carboxy, carboxyalkyl, carboxyalkylaryl; or $R^3$ is selected from the group consisting of H, alkyl, alkenyl, $CH_2OC(=O)YR^6$, alkylhydroxy, alkylpolyhydroxy, alkyl (poly)oxyacyl, alkylcarboxy, optionally substituted by one or more of alkyl, hydroxy, amino, carboxy, carboxyalkyl, alkylcarbonyl;

$R^4$ is selected from H, OH, SH, $OR^6$, $SR^6$, $OC(=O)R^6$, $SC(=O)R^6$, $CH_2OC(=O)YR^6$, $OC(=O)YR^6$, $SC(=O)YR^6$;

Y is independently selected from O, S, $CH_2$, $CHR^6$, $C(R^6)_2$, NH, $NR^6$;

$R^5$ is selected from H, OH, SH, $OR^6$, $SR^6$, $OC(=O)R^6$, $SC(=O)R^6$, $CH_2OC(=O)YR^6$, $OC(=O)YR^6$, $SC(=O)YR^6$;

provided that $R^4$ and $R^5$ are not simultaneously hydrogen or $CH_2OC(=O)YR^6$.

$R^6$ is selected from hydrogen, alkyl, alkenyl, alkynyl, cycloalkyl, heterocyclic, aryl, heteroaryl all optionally substituted by one or more alkyl, alkoxy, hydroxy, halogen, trifluoromethyl, nitro, cyano, or amino groups;

$R^7$ is selected from H, $S(O)R^9$, $SO_2R^9$, $CH_2OC(O)$—$R^9$, $C(O)$—$R^9$ where $C(O)$—$R^9$ can represent natural and synthetic amino acids or $R^9$ can be defined as below, or $R^7$ and $R^3$ taken together comprise a 5- or 6- membered heterocyclic ring containing two or more heteroatoms, optionally substituted with alkyl and/or oxygen functions including carbonyl, or taken together comprise a metal complex containing a divalent cation, or a boron complex;

$R^8$ is selected from H, acyl;

$R^9$ is selected from substituted dihydropyridyl, alkyl, thioalkoxy, alkoxy, amino, cycloalkoxy, optionally substituted with one or more of amino, alkyl, alkylaryl, heteroaryl, alkylheteroaryl, alkylmercaptoalkyl, which may optionally be substituted with one or more of hydroxy, amino, guanidino, iminoalkyl;

X is selected from the group consisting of lower alkylenes, lower alkenylenes and lower alkynylenes and which may optionally be substituted by one or more alkyl, alkoxy, hydroxy, halogen, trifluoromethyl, nitro, cyano, or amino groups; or X is selected from the group consisting of the formula —(CH$_2$)$_k$Q(CH$_2$)$_t$— where k is 1, 2 or 3, t is 1, 2 or 3 and Q is O (oxygen), Se, SiE$_2$ where E is lower alkyl, aryl, S(O)$_g$ where g is 0, 1 or 2, or NR where R is H or lower alkyl which may be optionally substituted with lower alkyl, lower alkoxy, hydroxy, halogen, trifluoromethyl, nitro, cyano, amino; or X is selected from the group consisting of the formula —(CH$_2$)$_m$T(CH$_2$)$_n$— where m is 0, 1 or 2, n is 0, 1 or 2, T is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

A preferred embodiment of the present invention is a compound of the formula (I):

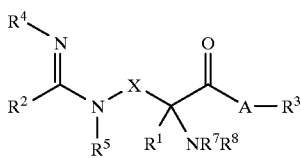

and pharmaceutically acceptable salts, wherein:

A is selected from O (oxygen) or S and may be taken together with $R^4$ to form a heterocyclic ring; or A is N when $R^3$ and $R^7$ are taken together to form a heterocyclic ring; or $R^5$ and A—$R^3$ are taken together to form a covalent bond; or A is N—$R^3$ provided $R^3$ is not a heterocyclic radical;

$R^1$ is selected from the group consisting of hydrogen, hydroxyalkyls of from 1 to 4 carbon atoms, alkoxyalkyls of from 1 to 4 carbon atoms in each position, lower alkyls of from 1 to 8 carbon atoms and haloalkyls of from 1 to 4 carbon atoms;

$R^2$ is selected from the group consisting of straight and branched lower alkyls of from 1 to 4 carbon atoms, lower alkenyls and lower alkynyls of from 2 to 4 carbon atoms, cycloalkyls of from 1 to 4 carbon atoms, cycloalkenyls of from 3 to 8 carbon atoms, and haloalkyls of from 1 to 4 carbon atoms;

$R^3$ is selected from the group consisting of aryl, heteroaryl, alkylaryl, alkylheteroaryl, all optionally substituted by one or more of halogen, nitrile, carboxy, carboxyalkyl, carboxyalkylaryl; or $R^3$ is also selected from the group consisting of H, alkyl of from 1 to 4 carbon atoms, alkenyl of from 2 to 4 carbon atoms, CH$_2$OC(=O)YR$^6$, alkylhydroxy, alkylpolyhydroxy, alkyl(poly)oxyacyl, alkylcarboxy, optionally substituted by one or more of alkyl of from 1 to 4 carbon atoms, hydroxy, amino, carboxy, carboxyalkyl, alkylcarbonyl;

$R^4$ is selected from H, OH, SH, OR$^6$, SR$^6$, OC(=O)R$^6$, SC(=O)R$^6$, CH$_2$OC(=O)YR$^6$, OC(=O)YR$^6$, SC(=O)YR$^6$;

Y is independently selected from O, S, CH$_2$, CHR$^6$, C(R$^6$)$_2$, NH, NR$^6$;

$R^5$ is selected from H, OH, SH, OR$^6$, SR$^6$, OC(=O)R$^6$, SC(=O)R$^6$, CH$_2$OC(=O)YR$^6$, OC(=O)YR$^6$, SC(=O)YR$^6$;

provided that $R^4$ and $R^5$ are not simultaneously hydrogen or CH$_2$OC(=O)YR$^6$.

$R^6$ is selected from hydrogen, alkyl of from 1 to 4 carbon atoms, alkenyl and alkynyl of from 2 to 4 carbon atoms, cycloalkyl of from 3 to 8 carbon atoms, heterocyclic of from 5 to 8 members, aryl, heteroaryl all optionally substituted by one or more alkyl of from 1 to 4 carbon atoms, alkoxy, hydroxy, halogen, trifluoromethyl, nitro, cyano, or amino groups;

$R^7$ is selected from H, S(O)R$^9$, SO$_2$R$^9$, CH$_2$OC(O)—R$^9$, C(O)—R$^9$ where C(O)—R$^9$ can represent natural and synthetic amino acids or $R^9$ can be defined as below, or $R^7$ and $R^3$ taken together comprise a 5- or 6- membered heterocyclic ring containing two or more heteroatoms, optionally substituted with alkyl of from 1 to 4 carbon atoms and/or oxygen functions including carbonyl, or taken together comprise a metal complex containing a divalent cation, or a boron complex;

$R^8$ is selected from H, acyl;

$R^9$ is selected from substituted dihydropyridyl, alkyl of from 1 to 4 carbon atoms, thioalkoxy, alkoxy, amino, cycloalkoxy, optionally substituted with one or more of amino, alkyl of from 2 to 4 carbon atoms, alkylaryl, heteroaryl, alkylheteroaryl, alkylmercaptoalkyl, which may optionally be substituted with one or more of hydroxy, amino, guanidino, iminoalkyl;

X is selected from the group consisting of alkylenes, alkenylenes and alkynylenes having 2 to 6 carbon atoms and which may optionally be substituted by one or more alkyl groups; or X is selected from the group consisting of the formula —(CH$_2$)$_k$Q(CH$_2$)$_t$— where k is 1, 2 or 3, t is 1, 2 or 3 and Q is O (oxygen), Se, SiE$_2$ where E is lower alkyl, aryl, S(O)$_g$ where g is 0, 1 or 2, or NR where R is H or lower alkyl which may be optionally substituted with lower alkyl, lower alkoxy, hydroxy, halogen, trifluoromethyl, nitro, cyano, amino; or X is selected from the group consisting of the formula —(CH$_2$)$_m$T(CH$_2$)$_n$— where m is 0, 1 or 2, n is 0, 1 or 2, T is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

A preferred embodiment of the present invention is a compound of the formula (I):

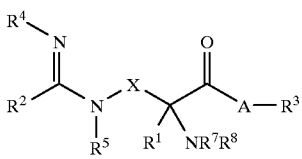

(I)

and pharmaceutically acceptable salts, wherein:

A is selected from O (oxygen) or S and may be taken together with $R^4$ to form a heterocyclic ring; or A is N when $R^3$ and $R^7$ are taken together to form a heterocyclic ring; or $R^5$ and A—$R^3$ are taken together to form a covalent bond; or A is N—$R^3$ provided $R^3$ is not a heterocyclic radical;

$R^1$ is selected from the group consisting of hydrogen, hydroxyalkyls of from 1 to 4 carbon atoms, alkoxyalkyls of from 1 to 4 carbon atoms in each position, lower alkyls of from 1 to 8 carbon atoms and haloalkyls of from 1 to 4 carbon atoms;

$R^2$ is selected from the group consisting of straight and branched lower alkyls of from 1 to 4 carbon atoms, lower alkenyls and lower alkynyls of from 2 to 4 carbon atoms, cycloalkyls of from 1 to 4 carbon atoms, cycloalkenyls of from 3 to 8 carbon atoms, and haloalkyls of from 1 to 4 carbon atoms;

$R^3$ is selected from the group consisting of aryl, heteroaryl, alkylaryl, alkylheteroaryl, all optionally substituted by one or more of halogen, nitrile, carboxy, carboxyalkyl, carboxyalkylaryl; or $R^3$ is also selected from the group consisting of H, alkyl of from 1 to 4 carbon atoms, alkenyl of from 2 to 4 carbon atoms, $CH_2OC(=O)YR^6$, alkylhydroxy, alkylpolyhydroxy, alkyl(poly)oxyacyl, alkylcarboxy;

$R^4$ is selected from H, OH, SH, $OR^6$, $SR^6$, $OC(=O)R^6$, $SC(=O)R^6$, $CH_2OC(=O)YR^6$;

Y is independently selected from O, S, $CH_2$, $CHR^6$, $C(R^6)_2$, NH, $NR^6$;

$R^5$ is selected from H, OH, SH, $OR^6$, $SR^6$, $OC(=O)R^6$, $SC(=O)R^6$, $CH_2OC(=O)YR^6$;

provided that $R^4$ and $R^5$ are not simultaneously hydrogen.

$R^6$ is selected from hydrogen, alkyl of from 1 to 4 carbon atoms, alkenyl and alkynyl of from 2 to 4 carbon atoms, cycloalkyl of from 3 to 8 carbon atoms, heterocyclic of from 5 to 8 members, aryl, heteroaryl all optionally substituted by one or more alkyl of from 1 to 4 carbon atoms or hydroxy groups;

$R^7$ is selected from H, $S(O)R^9$, $SO_2R^9$, $CH_2OC(O)$—$R^9$, $C(O)$—$R^9$ where $C(O)$—$R^9$ can represent natural and synthetic amino acids or $R^9$ can be defined as below, or $R^7$ and $R^3$ taken together comprise a 5- or 6- membered heterocyclic ring containing two or more heteroatoms;

$R^8$ is selected from H, acyl;

$R^9$ is selected from substituted dihydropyridyl, alkyl of from 1 to 4 carbon atoms, thioalkoxy, alkoxy, amino, cycloalkoxy;

X is selected from the group consisting of alkylenes, alkenylenes and alkynylenes having 2 to 6 carbon atoms and which may optionally be substituted by one or more alkyl groups; or X is selected from the group consisting of the formula —$(CH_2)_kQ(CH_2)_t$— where k is 2 or 3, t is 1 or 2 and Q is O (oxygen), Se, $SiE_2$ where E is lower alkyl, aryl, $S(O)_g$ where g is 0, 1 or 2, or NR where R is H or lower alkyl which may be optionally substituted with lower alkyl; or X is selected from the group consisting of the formula —$(CH_2)_mT(CH_2)_n$— where m is 0, 1 or 2, n is 0, 1 or 2, T is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

Another preferred embodiment of the present invention is a compound of the formula (I) and pharmaceutically acceptable salts; wherein:

A is selected from O (oxygen) and may be taken together with $R^4$ to form a heterocyclic ring; or A when $R^5$ and A—$R^3$ are taken together forms a covalent bond;

A is N—$R^3$ where the $R^3$ radicals are selected from hydrogen, alkyl of from 1 to 4 carbon atoms or aryl;

$R^1$ is selected from the group consisting of hydrogen, hydroxyalkyls of from 1 to 4 carbon atoms and lower alkyls of from 1 to 8 carbon atoms;

$R^2$ is selected from the group consisting of straight and branched lower alkyls of from 1 to 4 carbon atoms and haloalkyls of from 1 to 4 carbon atoms;

$R^3$ is selected from the group consisting of aryl, heteroaryl, alkylaryl, alkylheteroaryl, all optionally substituted by one or more of halogen, nitrile, carboxy, carboxyalkyl, carboxyalkylaryl; or $R^3$ is also selected from the group consisting of H, alkyl of from 1 to 4 carbon atoms and alkenyl of from 2 to 4 carbon atoms;

$R^4$ is selected from H, OH, SH, $OR^6$, $SR^6$;

$R^5$ is selected from H, OH, SH, $OR^6$, $SR^6$;

provided that $R^4$ and $R^5$ are not simultaneously hydrogen.

$R^6$ is selected from hydrogen, alkyl of from 1 to 4 carbon atoms, alkenyl and alkynyl of from 2 to 4 carbon atoms and cycloalkyl of from 3 to 8 carbon atoms;

$R^7$ is selected from H and where $C(O)$—$R^9$ can represent natural and synthetic amino acids;

$R^8$ is selected from H and acyl;

X is selected from the group consisting of alkylenes, alkenylenes and alkynylenes having 2 to 6 carbon atoms and which may optionally be substituted by one or more alkyl groups; or X is selected from the group consisting of the formula —$(CH_2)_kQ(CH_2)_t$— where k is 2 or 3, t is 1 or 2 and Q is O (oxygen), $S(O)_g$ where g is 0, 1 or 2, or NR where R is H or lower alkyl or X is selected from the group consisting of the formula —$(CH_2)_mT(CH_2)_n$— where m is 0, 1 or 2, n is 0, 1 or 2, T is a 3 to 6 membered carbocyclic or heterocyclic ring, aromatic ring or heteroaromatic ring.

Another preferred embodiment of the present invention is a compound of the formula (I) and pharmaceutically acceptable salts; wherein:

A is O (oxygen);

$R^1$ is hydrogen;

$R^2$ is methyl;

$R^3$ is selected from the group consisting of hydrogen, and lower alkyls of 1 to about 4 carbon atoms;

$R^4$ is hydroxy;

$R^5$ is hydrogen or hydroxy;

$R^7$ is hydrogen;

$R^8$ is hydrogen;

X is an alkylene having 3 to 5 carbon atoms.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, fumaric, maleic, oxaloacetic, methanesulphonic, ethanesulphonic, p-toluenesulphonic, benzenesulphonic and isethionic acids. Salts of the compounds of formula (I) can be made by reacting the appropriate compound in the form of the free base with the appropriate acid.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, pentenylen-1-yl, 2-2-methylbuten-1-yl, 3-methylbuten-1-yl, hexen-1-yl, hepten-1-yl, and octen-1-yl, and the like.

The term "lower alkynyl", refers to an unsaturated acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "heterocyclic radical" means an unsaturated cyclic hydrocarbon radical with 3 to about 6 carbon atoms, wherein 1 to about 4 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazonyl, quinolinyl, and the like.

The term "aryl" means an aromatic hydrocarbon radical of 6 to about 14 carbon atoms, preferably 6 to about 10 carbon atoms. Examples of suitable aromatic hydrocarbon radicals include phenyl, naphthyl, and the like.

The terms "cycloalkyl" or "cycloalkenyl" means an "alicyclic radical in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The terms "lower alkylene", "lower alkenylenes" and "lower alkynylene" refers to hydrocarbons containing 2 to 10 carbon atoms, preferably 2 to 8 carbon atoms, and more preferably 2 to 6 carbon atoms.

The term "halogen" means fluorine, chlorine, bromine or iodine.

The term "prodrug" refers to a compound that is made more active in vivo.

As used herein, reference to "treatment" of a patient is intended to include prophylaxis.

All references, patents or applications, U.S. or foreign, cited in the application are hereby incorporated by reference as if written herein.

The following general synthetic sequences are useful in making the present invention. Abbreviations used in the schemes are as follows: "Boc" represents tert-butyloxycarbonyl, "Z" or "bcz" represents benzyloxycarbonyl "Fmoc" represents 9-fluorenylmethoxycarbonyl, "DIPEA" represents diisopropylethylamine, "DMF" represents dimethylformamide, and "TBTU" represents 2-(1H-benzotriozole-1-yl)-1,1,3,3-tetramethyl uronium tetrafluoroborate.

Scheme 1

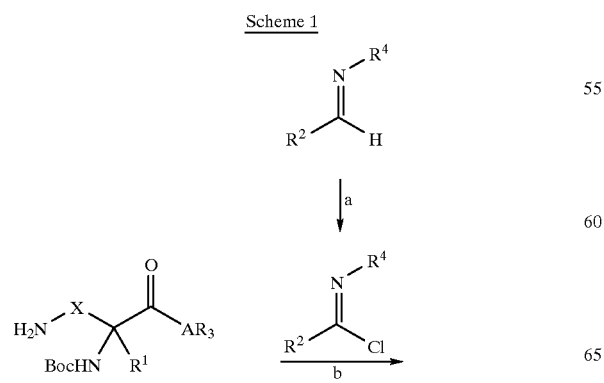

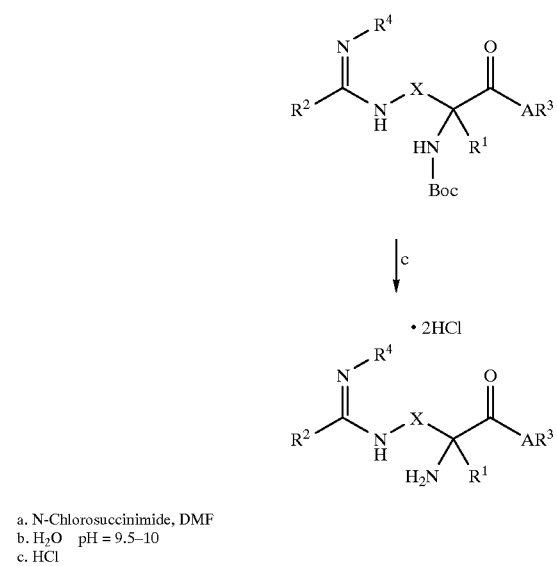

a. N-Chlorosuccinimide, DMF
b. H₂O   pH = 9.5–10
c. HCl

Scheme 2

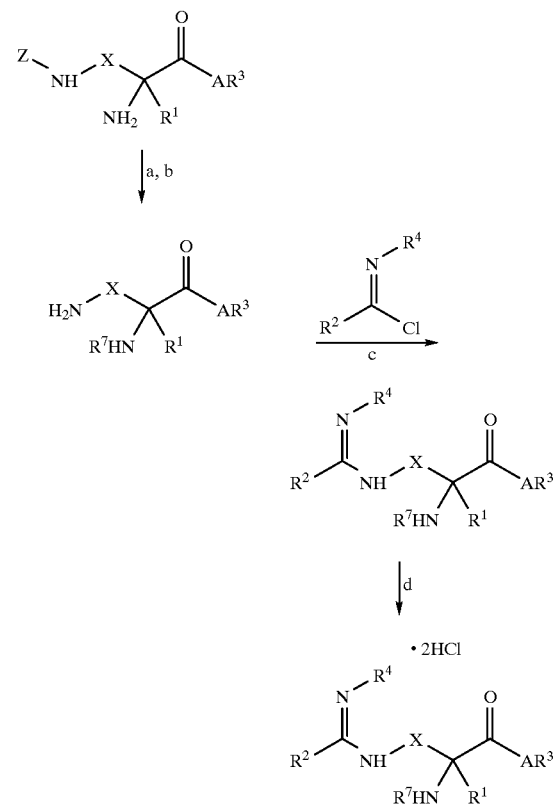

a. acid chloride or chloroformate or isocyanate or sulfonyl chloride or sulfinyl chloride
b. hydrogenation
c. H₂O   pH = 9.5–10
d. HCl Scheme 3
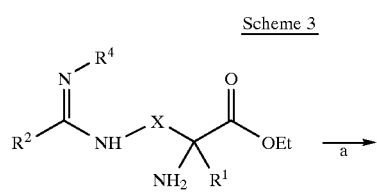
a. $R^9CO_2H$ TBTU/DIPEA/DMF
b. hydrolysis
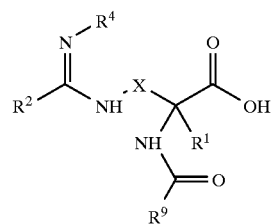
Scheme 4

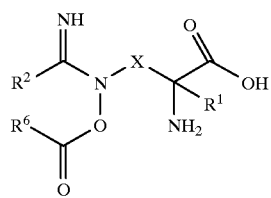
a. $R^2C(OEt)=NH$
b. HBr/AcOH or catalytic hydrogenation followed by hydrolysis
c. acid chloride
Scheme 5
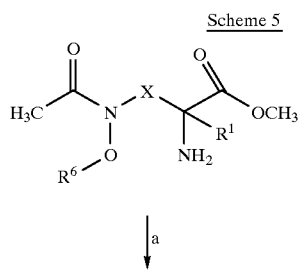
↓ a
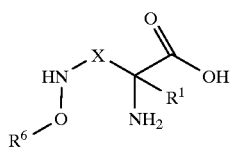
↓ b, c, d
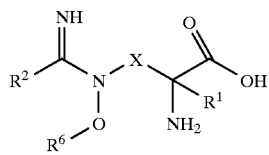
a. hydrolysis
b. $CuCO_3$
c. $R^2C(OEt)=NH$
d. Dowex 50
Scheme 6
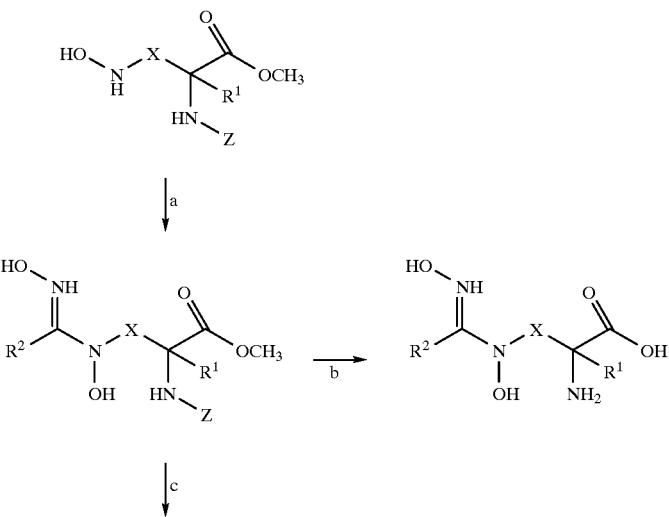

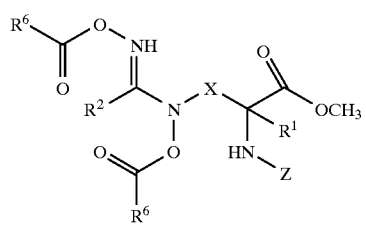
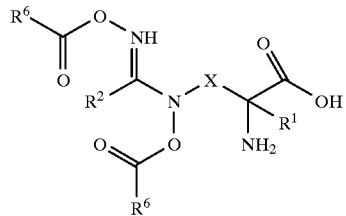
a. R²C(Cl) = NOH
b. HBr/AcOH or
   hydrogenation followed by hydrolysis
c. acid chloride
Scheme 7
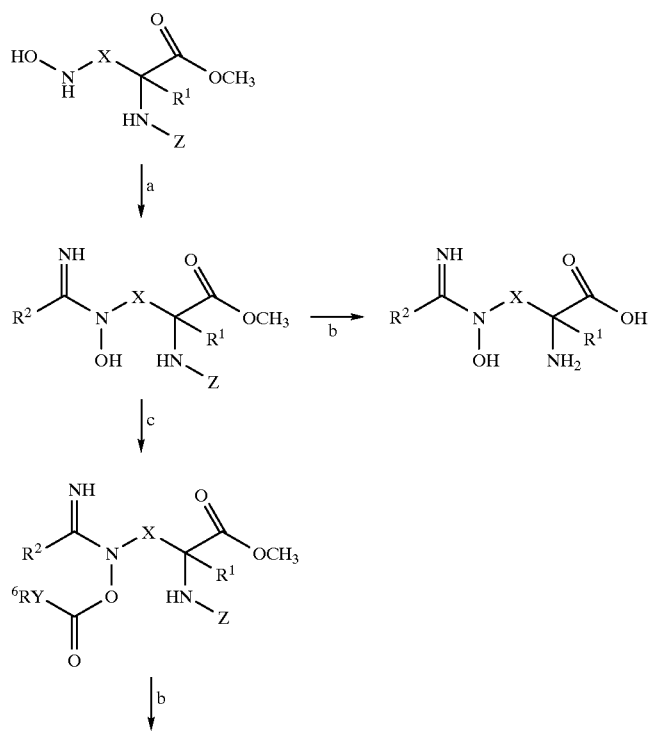

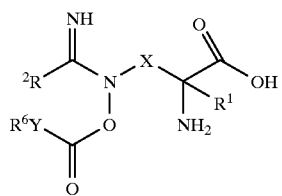
a. R²C(OEt)=NH
b. HBr/AcOH or hydrogenation followed by hydrolysis
c. acid chloride or chloroformate or isocyanate
Scheme 8
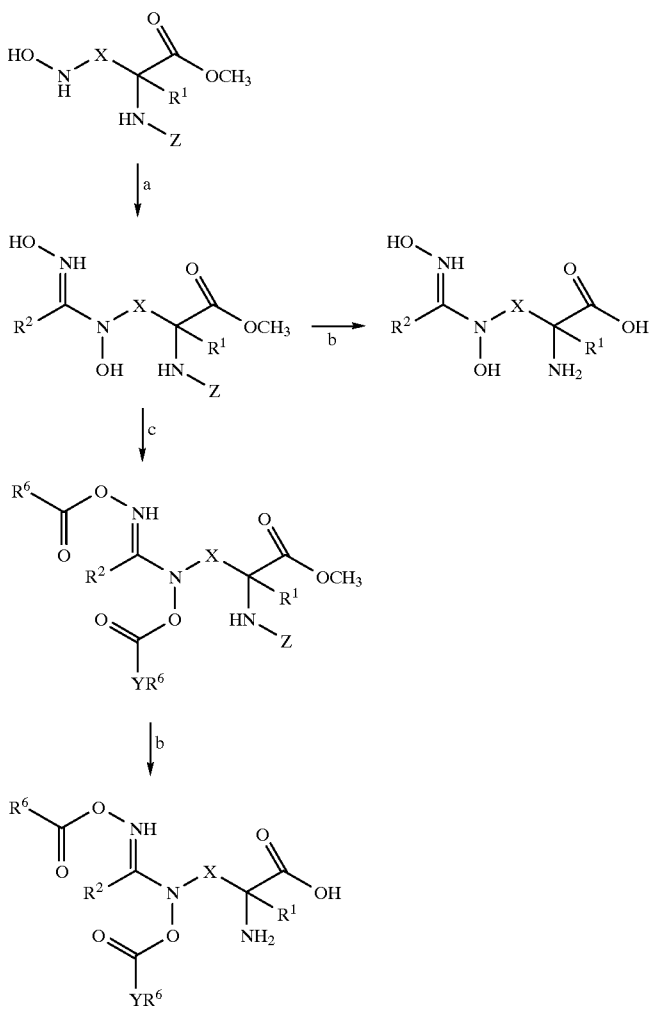
a. R²C(Cl)=NOH
b. HBr/AcOH or hydrogenation followed by hydrolysis
c. acid chloride or chloroformate or isocyanate

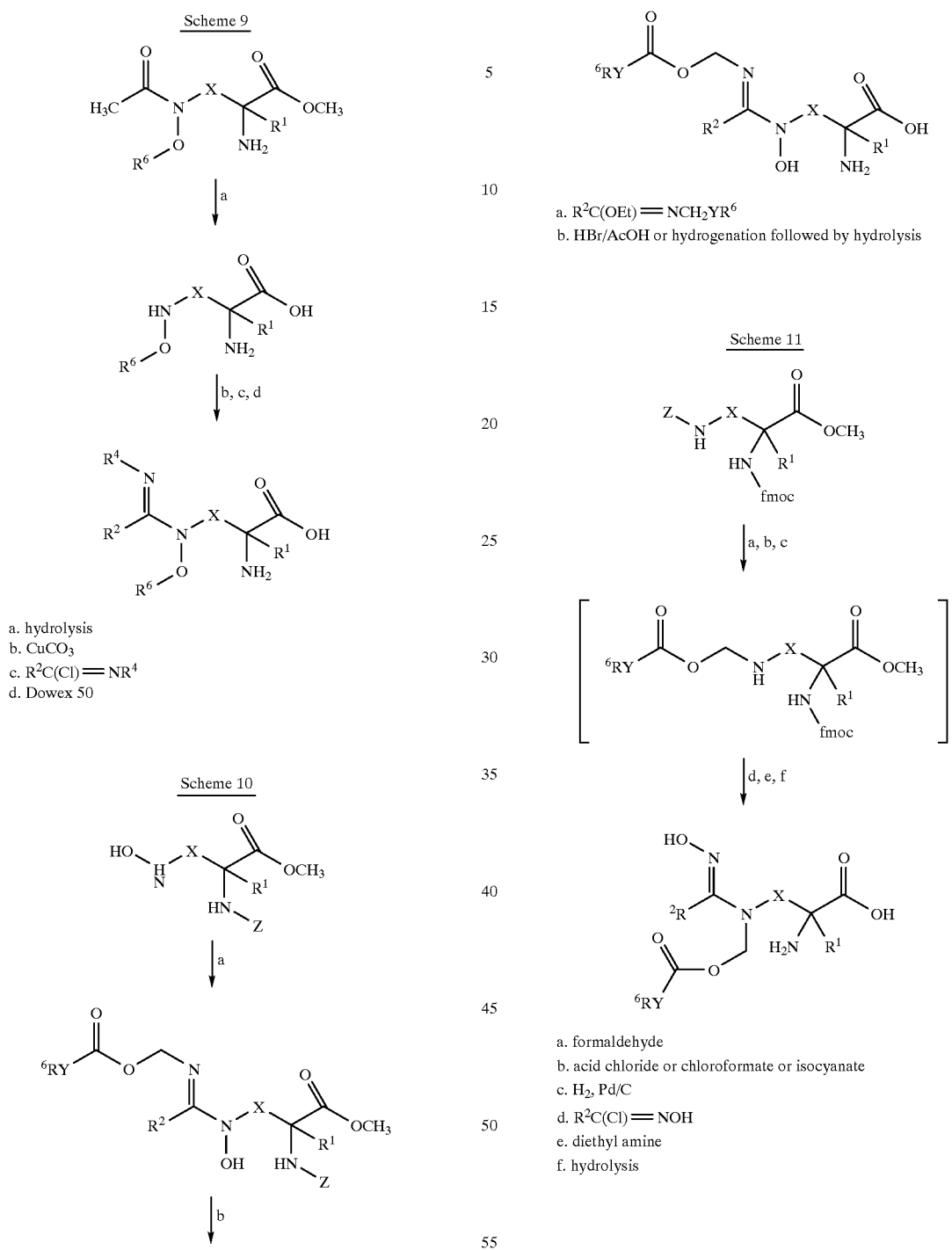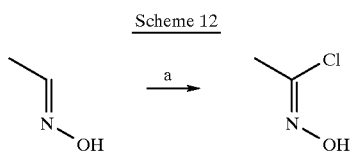

5,981,511
23
24
-continued
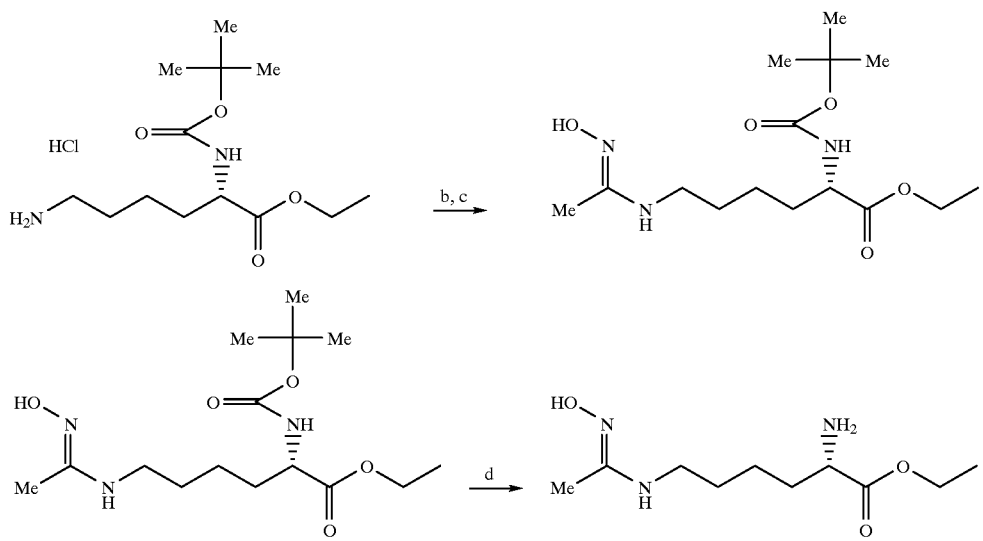
a. N-chlorosuccinimide
b. chloroacetaldoxime, pH 8.5
c. cation exchange resin
d. HCl/EtOH
Scheme 13
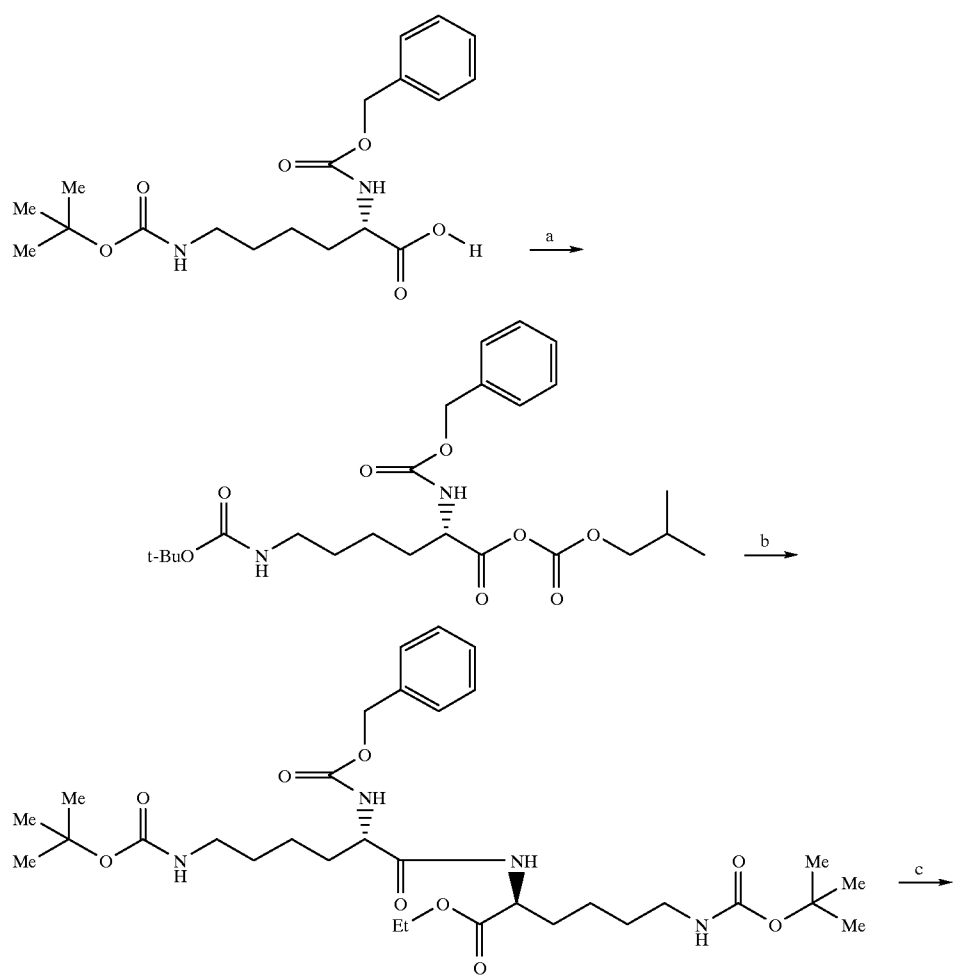

-continued
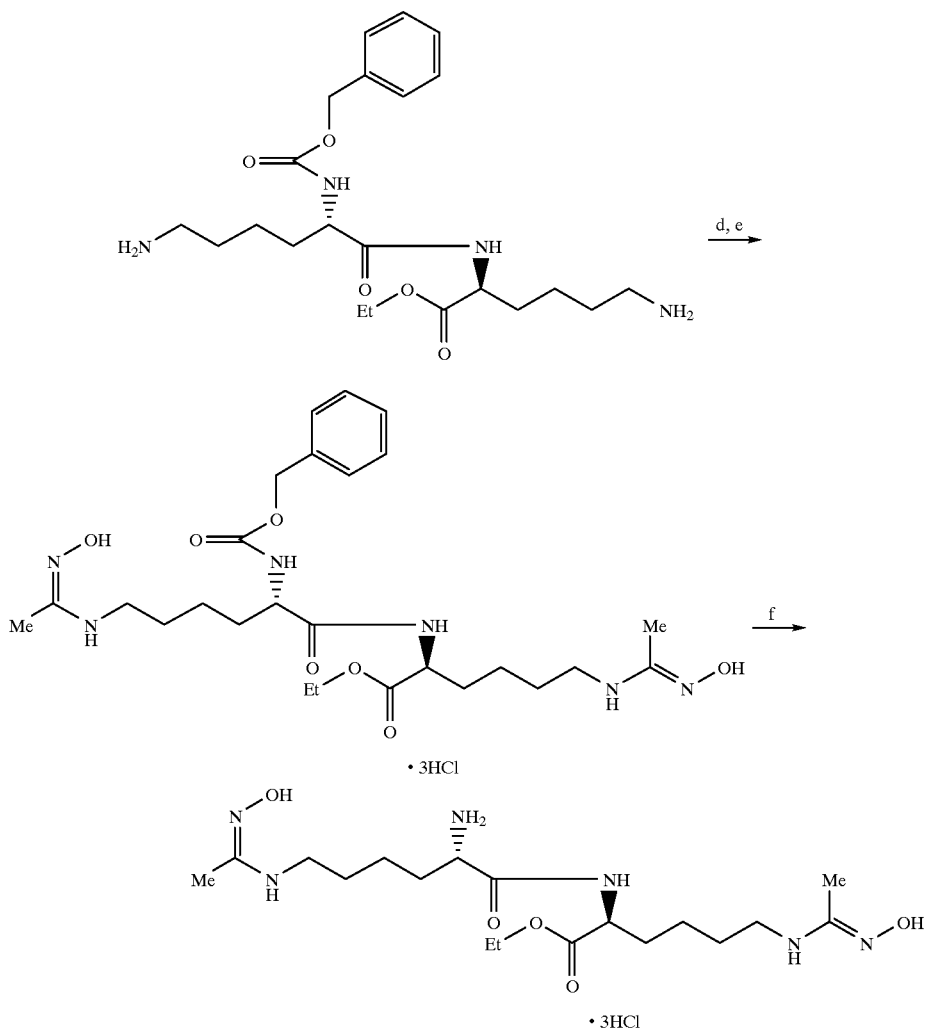
a. isobutylchloroformate/N-methylmorpholine (NMM)/DMF/dichloromethane (DCM)
b. ε-Boc-L-Lys-OEt HCl/NMM/DMF
c. HCl/EtOH
d. chloroacetaldoxime, pH 8.5
e. cation exchange resin
f. Pd/C/EtOH/HCl
Scheme 14
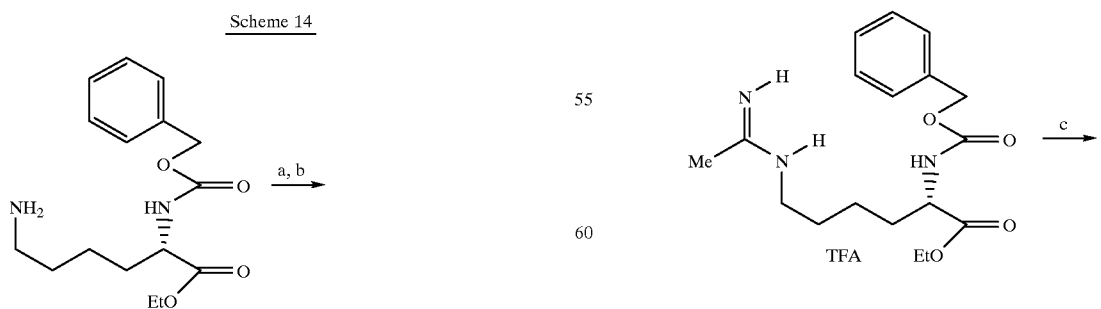
-continued

27

-continued

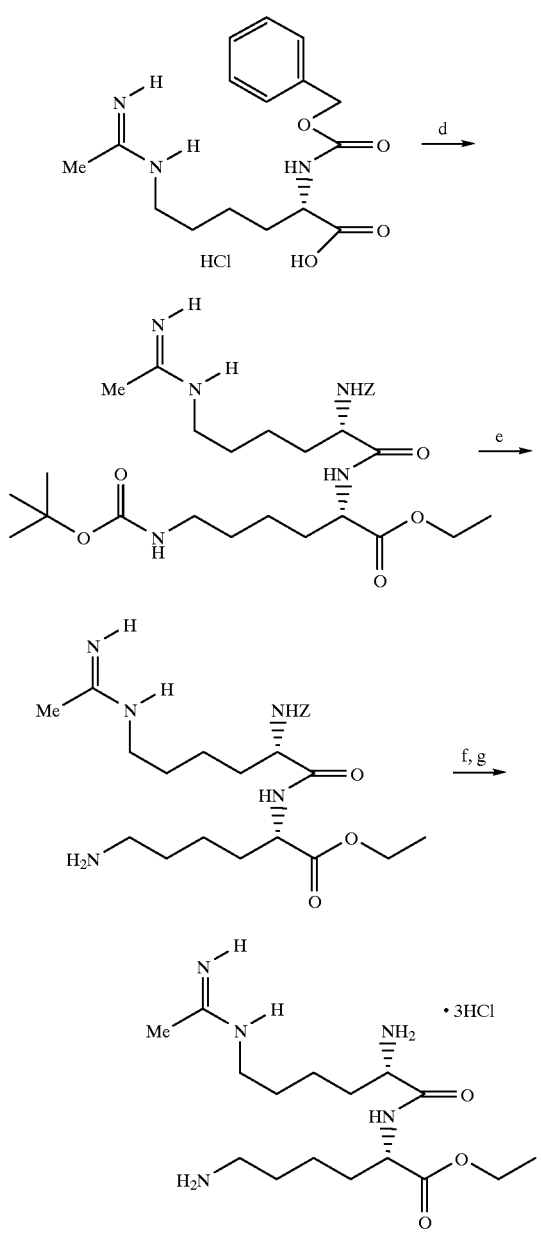

a. methyl acetimidate/N,N-diisopropylethylamine/DMF
b. reverse phase column chromatograpy
c. hydrolysis, chloride anion exchange column if necessary
d. ε–Boc-L-Lys-OEt/1-hydroxybenzotriazole
 hydrate/DMF/[(N,N-dimethylamino)propyl]ehtylcarbodiimide
 hydrochloride, then reverse phase column chromatograpy
e. 4N HCl/EtOH
f. chloroacetaldoxime, pH 8.5, then cation exchange resin
g. Pd/C/EtOH/HCl

28

Scheme 15

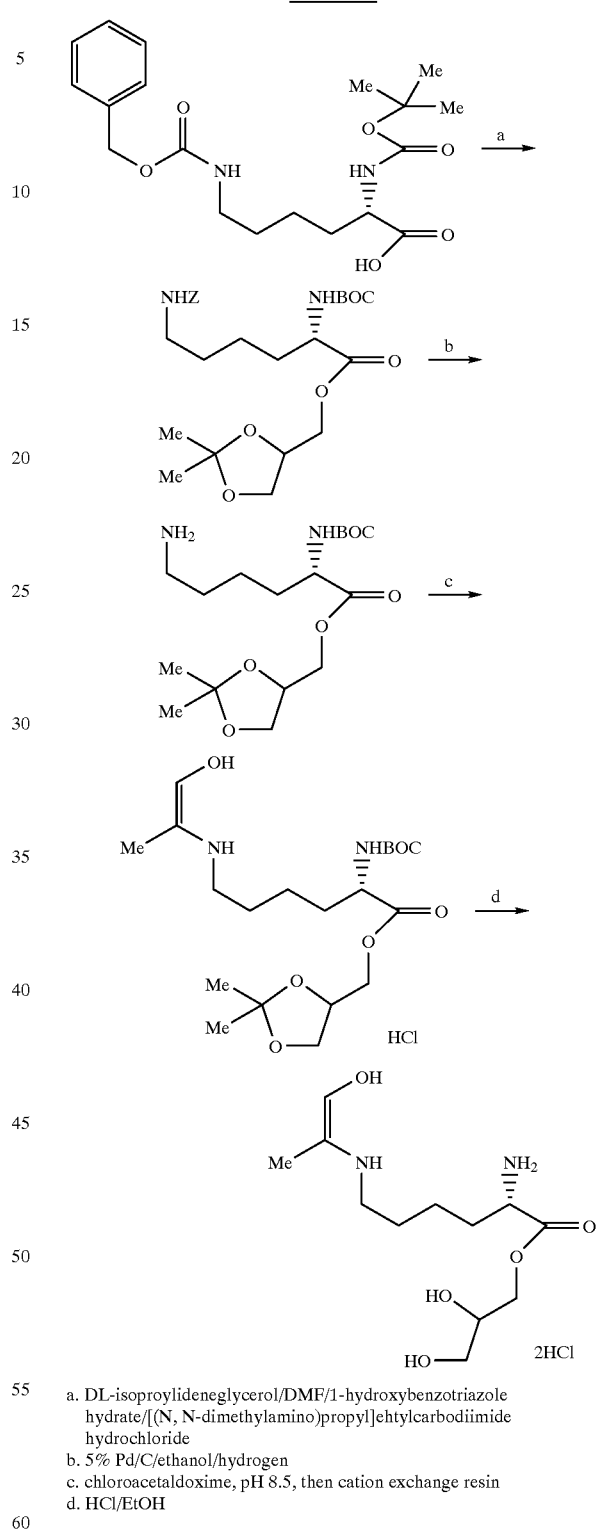

a. DL-isoproylideneglycerol/DMF/1-hydroxybenzotriazole
 hydrate/[(N, N-dimethylamino)propyl]ehtylcarbodiimide
 hydrochloride
b. 5% Pd/C/ethanol/hydrogen
c. chloroacetaldoxime, pH 8.5, then cation exchange resin
d. HCl/EtOH

Scheme 16
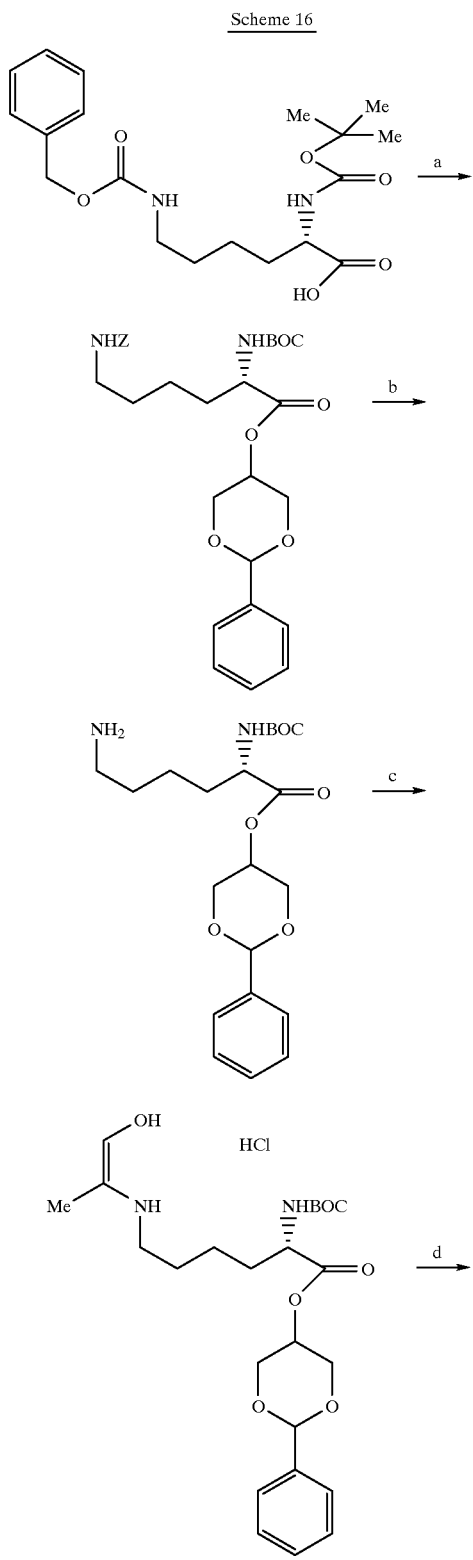
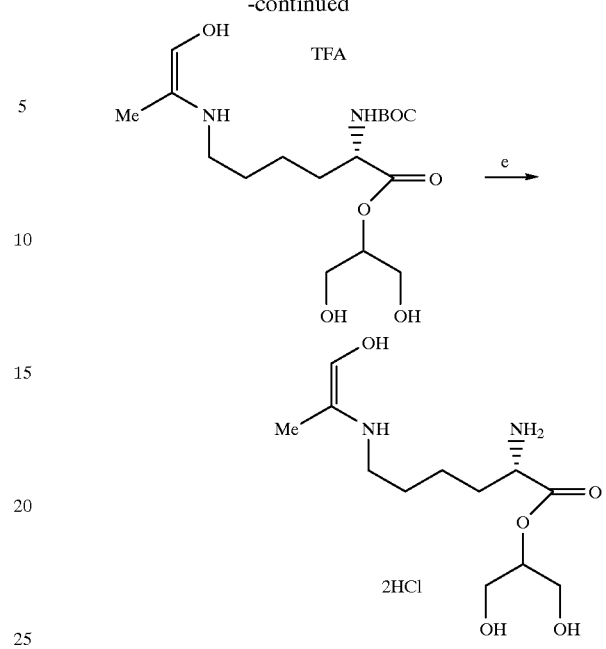
a. 1,3-benzylideneglycerol/DMF/1-hydroxybenzotriazole hydrate/[N, N-dimethylamino)propyl]ethylcarbodiimide hydrochloride
b. 5% Pd/C/ethanol/hydrogen
c. chloroacetaldoxime, pH 8.5
d. H₃BO₃/(EtO)₃B, reverse phase column chromatography
e. HCl
Scheme 17
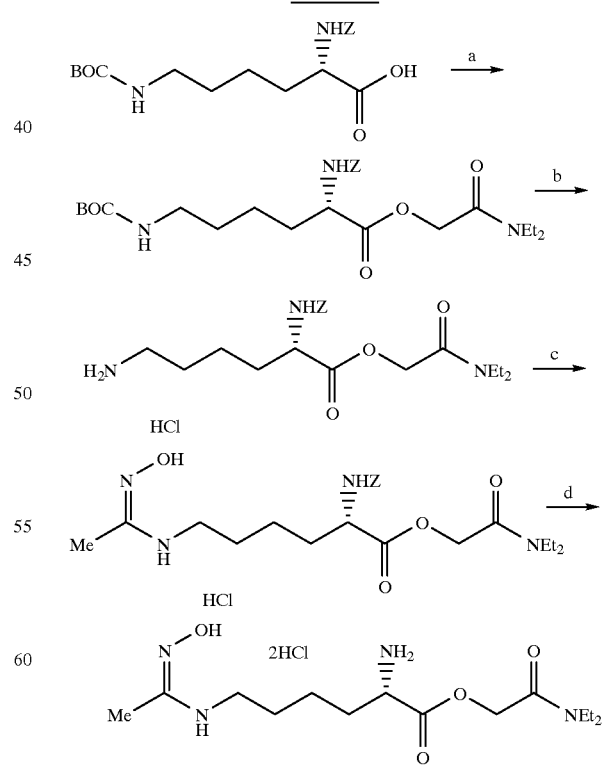

-continued a. 2-chloro-N, N-diethylacetamide/triethylamine/NaI
b. HCl/HOAc
c. chloroacetaldoxime, pH 8.5, then cation exchange resin
d. 5% Pd/C/ethanol/hydrogen/HCl

Scheme 18

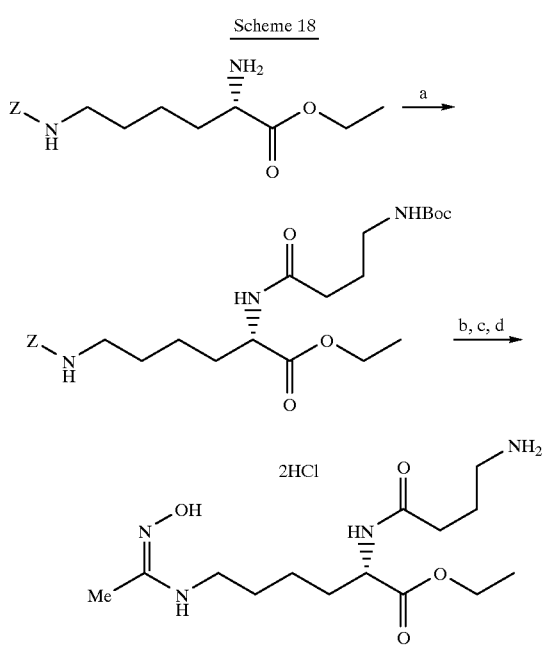

a. N-Boc-γ-aminobutyric acid/1-hydroxybenzotriazole hydrate/DMF)/[(N,N-dimethylamino)propyl]-ethylcarbodiimide hydrochloride
b. 5% Pd/C/ethanol/hydrogen
c. chloroactaldoxime, pH 8.5, then cation exchange resis
d. HCl/EtOH

Scheme 19

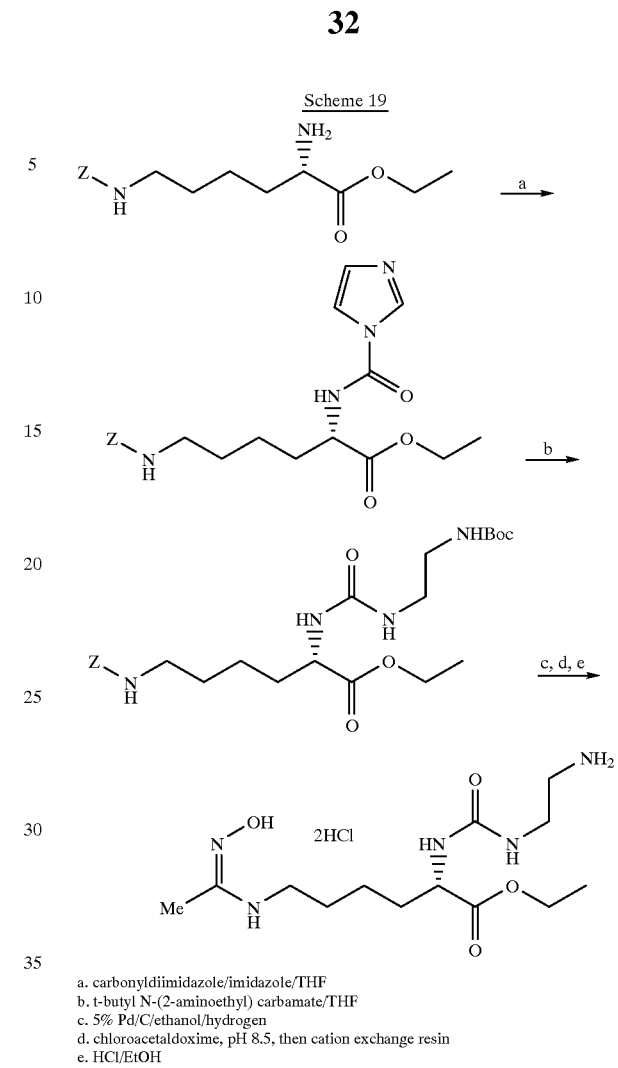

a. carbonyldiimidazole/imidazole/THF
b. t-butyl N-(2-aminoethyl) carbamate/THF
c. 5% Pd/C/ethanol/hydrogen
d. chloroacetaldoxime, pH 8.5, then cation exchange resin
e. HCl/EtOH

Scheme 20

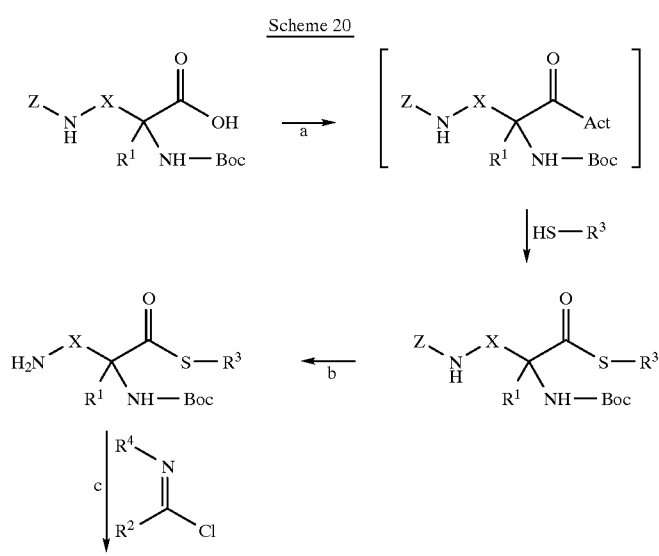

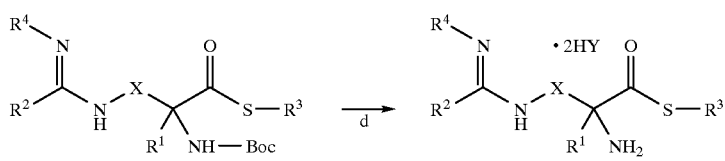

Act = amino acid activating group;
Y = pharmaceutically acceptable counter ion;
a) reagent(s) required to activate carbonyl to displacement by a nucleophile;
b) $H_2$ and catalyst;
c) base;
d) HCl in solvent such as dioxane.

Scheme 21

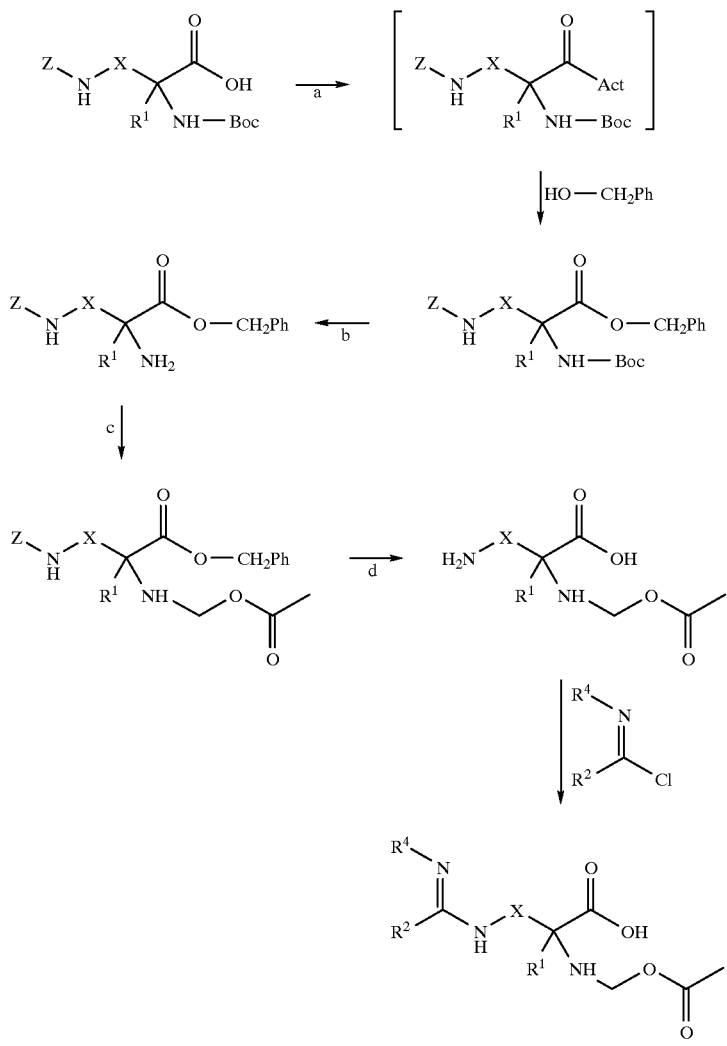

Act = amino acid activating group;
Y = pharmaceutically acceptable counter ion;
a) reagent(s) required to activate carbonyl to displacement by a nucleophile;
b) HCl in solvent such as dioxane;
c) formaldehyde, $Cs_2CO_3$, acetic anhydride;
d) H2 and catalyst.

Scheme 22
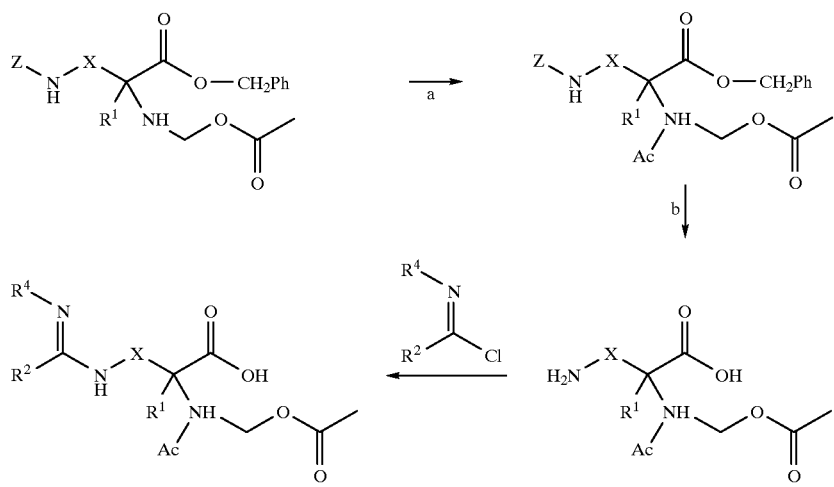
Act = amino acid activating group;
Y = pharmaceutically acceptable counter ion;
a) Cs₂CO₃, acetic anhydride;
b) H₂ and catalyst.
Scheme 23
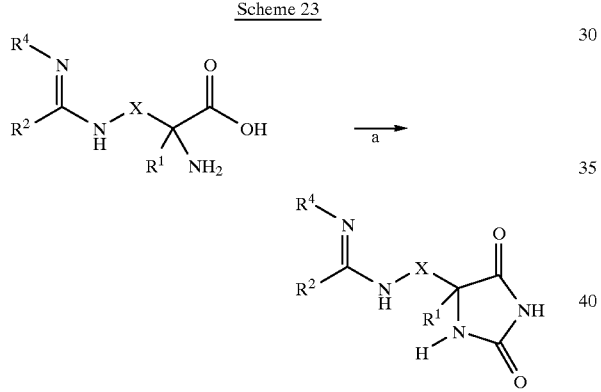
a) potassium cyanate, HCl (aq) [see Bull. Soc. Chim. Fr. 1954, 812, 815].
Scheme 24
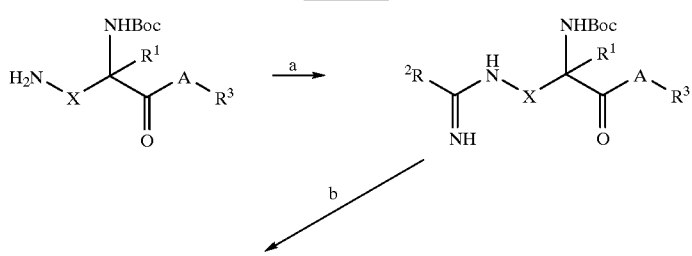

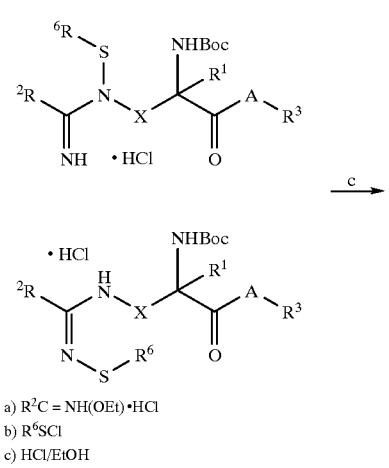
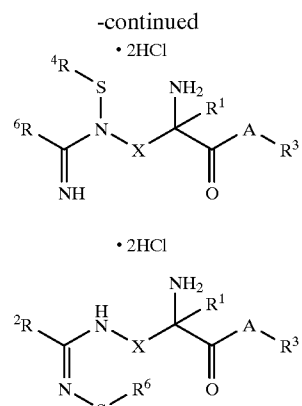

a) R²C = NH(OEt)·HCl
b) R⁶SCl
c) HCl/EtOH

Scheme 25

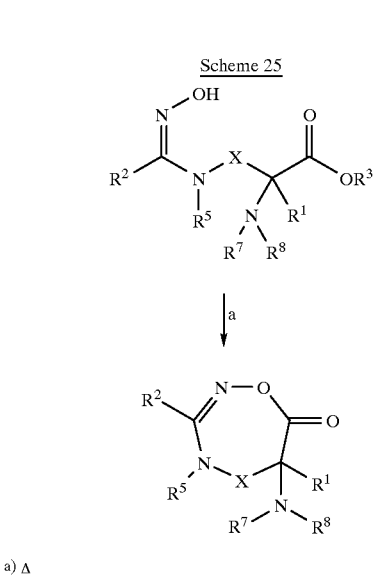

a) Δ

Scheme 26

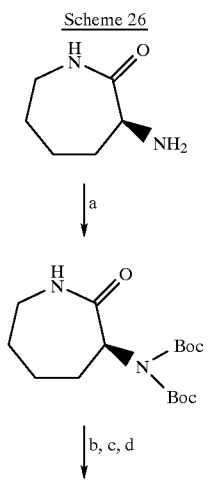

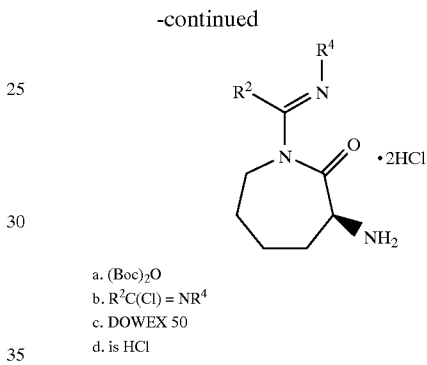

a. (Boc)₂O
b. R²C(Cl) = NR⁴
c. DOWEX 50
d. is HCl

Without further elaboration, it is believed that one skilled in the art can, using the preceding descriptions, utilize the present invention to its fullest extent. Therefore the following preferred specific embodiments are to be construed as merely illustrative and not limitative of the remainder of the disclosure in any way whatsoever. Compounds containing multiple variations of the structural modifications illustrated in the preceding schemes or the following Examples are also contemplated.

All experiments were performed under either dry nitrogen or argon. All solvents and reagents were used without further purification unless otherwise noted. The routine work-up of the reactions involved the addition of the reaction mixture to a mixture of either neutral, or acidic, or basic aqueous solutions and organic solvent. The aqueous layer was extracted n times (x) with the indicated organic solvent. The combined organic extracts were washed n times (x) with the indicated aqueous solutions, dried over anhydrous $Na_2SO_4$, filtered, concentrated in vacuo, and purified as indicated. Separations by column chromatography were achieved with conditions described by Still. (Still, W. C.; Kahn, M.; Mitra, A. Rapid Chromatograhic Technique for Preparative Separation with Moderate Resolution. *J. Org. Chem.,* 1978, 43, 2923–2925.) The hydrochloride salts were made from 1N HCl, HCl in ethanol (EtOH), 2 N in MeOH, or 6 N HCl in dioxane. Thin layer chromatograms were run on 0.25 mm EM precoated plates of silica gel 60 F254. High performance liquid chromatograms (HPLC) were obtained from C-8 or C-18 reverse phase columns which were obtained from several vendors. Analytical samples were dried in an Abderhalden apparatus at either 56° C. or 78° C. ¹H NMR spectra were obtained from either General Electric QE-300 or Varian VXR 400 MHz spectrometer. ¹³C NMR spectra were obtained from a Varian spectrometer at 125.8 MHz.

EXAMPLE 1
N⁶-[1-(hydroxyimino)ethyl]-L-lysine, dihydrochloride

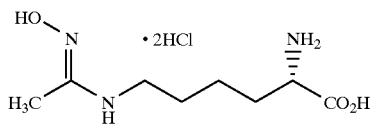

EX-1A) To a 125 mL flask was added 3 g (0.012 mol) of α-Boc-L-lysine and 70 mL of water. This solution was adjusted to pH=9.5 by addition of 2.5 N NaOH. To this solution was added portion wise, 2.3 g of chloroacetaldoxime which was prepared immediately prior to use by the reaction of 3.55 g (0.06 mol) of acetaldoxime with 10.4 g (0.78 mol) of N-chlorosuccinimide in 65 mL of N,N-dimethylformamide at 0° C. The chloroacetaldoxime was isolated after three hours by extracting into diethyl ether and washing with aqueous NaCl. Drying with MgSO₄, filtration and concentration under 30° C. afforded the chloroacetaldoxime as a pale yellow oil. During the chloroacetaldoxime addition, the pH was kept at 9.5 via concomitant addition of 2.5 N NaOH. After the addition was complete, the solution was allowed to stand at 25° C. for 25 minutes. The solution was then adjusted to pH=7.5 with 1N HCl and poured onto a Dowex 50 Cation exchange column. The column was washed with water. The Boc-protected product was then eluted with 10% aqueous pyridine.

EX-1) After concentrating, the product was deprotected by allowing it to stand in 2N HCl at 25° C. for two hours. Concentrating in vacuo afforded 2.9 g (78%) of L-N⁶-(oximinoethyl)lysine dihydrochloride as a viscous yellow oil. ¹H-NMR(D₂O) 1.25–1.45 (m, 2 H), 1.5–1.6 (m, 2 H), 1.75–1.9 (m, 2 H), 2.05 (s, 3 H), 3.25 (t, 2 H), 3.95 (t, 1H); Mass Spectra, M+H=204.

EXAMPLE 2
2-amino-5-[[1-(hydroxyimino)ethyl]amino]-2-methylpentanoic acid, dihydrochloride

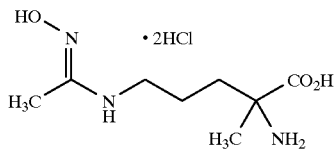

α-Methyl-D,L-ornithine hydrochloride is protected as a copper complex via reaction with cupric carbonate in water at reflux. This protected amino acid is then reacted with chloroacetaldoxime as in Example 1. The product is eluted from Dowex with 1N ammonium hydroxide. Concentration in vacuo, followed by acidification with hydrochloric acid affords the title compound.

EXAMPLE 3
N6-[1-(hydroxyimino)ethyl]-2-methyl-lysine, dihydrochloride

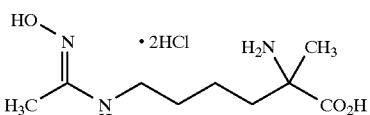

EX-3A) A suspension of lysine ethyl ester dihydrochloride (33 g; 0.14 mole) and MgSO₄ (34 g; 0.28 moles) in a solution of 4-chloro-benzaldehyde (39 g; 0.28 moles) and acetonitrile (500 mL) was stirred while N,N-diisopropylethylamine (36 g; 0.28 moles) was added in portions over ½ h. The mixture was stirred for 12 h, filtered, concentrated to a small volume, and diluted with 500 mL of diethyl ether. The ether solution was washed with 0.1% aqueous NaHCO₃, aqueous 2 N NaOH containing 2 g/100 ml of NH₂OH.HCl, again with 0.1% aqueous NaHCO₃ and saturated aqueous NaCl. After drying with MgSO₄ and removal of the solvent in vacuo, ethyl N, N'-di(4-chlorophenylmethylene)-L-lysine was obtained as a clear liquid.

EX-3B) The liquid was triturated with hexanes and the resulting solid was washed with hexanes. This partially purified intermediate was dissolved in 200 mL of THF and stirred in an acetone/dry ice bath. Sodium bis-(trimethylsilyl)amide in THF (11 mL, 1 M solution) was added dropwise over 30 min. After one hour, methyl iodide (0.8 g; 13 mmoles) in THF was added dropwise. The reaction mixture was slowly warmed up to room temperature and stirred overnight. The mixture was diluted with water, and extracted with ethyl ether. The ether extract was washed with 0.1% aqueous NaHCO₃ and saturated aqueous NaCl and concentrated to yield crude ethyl N,N'-di(4-chloro-phenylmethylene)-α-methyl-D,L-lysine (M+H=434).

EX-3C) This material (4 g) was dissolved in ethyl ether (100 ml) was stirred vigorously with 1 N HCl (50 mL) for 2 h, the layer was separated and the aqueous phase was washed with ethyl ether. The aqueous solution was further acidified by the addition of concentrated HCl to 6 N and was heated to reflux for 16 h. The solution was cooled to room temperature, and rotary evaporated to dryness. The residue was dissolved in water and applied to a Dowex 50×4 (hydrogen form).The column was washed with water, and then 10% pyridine. α-Methyl-D,L-lysine, (M+H=161) was eluted from the column with 1 M NH₄OH.

EX-3D) The α-methyl-D,L-lysine is protected as a copper complex via reaction with cupric carbonate in refluxing water.

EX-3) This protected amino acid is then reacted with chloroacetaldoxime as described in Example 1. The product is eluted from Dowex with 1N ammonium hydroxide. Concentration in vacuo, followed by acidification with hydrochloric acid affords the title compound.

EXAMPLE 4
2-[[2-[[1-(hydroxyimino)ethyl]amino]ethylseleno]methyl]-L-alanine, dihydrochloride

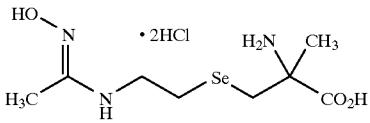

EX-4A) D,L-Selenocystine (117 mg; 0.5 mmoles, purchased from Sigma) was suspended in 15 mL of nitrogen (N₂) gas-purged water. Sodium borohydride (38 mg; 1 mole) was added. The reaction mixture became clear in a few minutes. After 2 h at room temperature, 2-bromoethylamine HCl (1.2 g; 6 mmoles) was added and the reaction mixture was stirred for 12 h. The reaction was applied on to a Dowex 50×4 (hydrogen form) column. The column was washed with water and 10% pyridine and 2-aminoethyl-selenocysteine was eluted with 1 M NH₄OH.

EX-4B) The 2-aminoethyl-selenocysteine is protected and subsequently methylated as described in Example 3 to afford the α-methyl-(2-aminoethyl)selenocysteine.

EX-4C) The α-methyl-(2-aminoethyl) selenocysteine is protected as a copper complex via reaction with cupric carbonate in refluxing water.

EX-4) This protected amino acid is then reacted with chloroacetaldoxime as described in Example 1. The product is eluted from Dowex with 1N ammonium hydroxide. Concentration in vacuo, followed by acidification with hydrochloric acid affords the title compound.

EXAMPLE 5

N⁶-[1-(hydroxyimino)ethyl]-2-(hydroxymethyl)-lysine, dihydrochloride

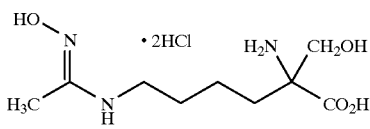

EX-5A) To an ice-cold stirred mixture of N^ε-Cbz-L-lysine (14 g; 0.05 moles, purchased from Sigma) in 2.5 N NaOH (24 mL), benzoyl chloride (10 g) was added gradually. The pH of the solution was maintained at 10.5–10.9 by addition of 2 N NaOH. The mixture was stirred at room temperature for 1 h and filtered. The filtrate was extracted with a small amount of ethyl acetate and the organic layer was dried over sodium sulfate. The solid was removed by filtration and the filtrate was evaporated to dryness.

EX-5B) The crude oily N^ε-Cbz-N^α-benzoyl-lysine residue (6 g) was heated at 90–100° C. in acetic anhydride (100 mL) for 30 min. The mixture was then evaporated. The residue was dissolved in pyridine and treated with aqueous formaldehyde (35% solution, Fisher). The mixture was stirred for 8 hr and then diluted. The reaction mixture was kept at 10° C. overnight. The precipitated crude material was hydrolyzed by boiling in 5 N HCl for 5 h. The reaction mixture was cooled and filtered before being evaporated. The solid residue was dissolved in water and passed through Dowex 50×4 (hydrogen form) column. α-Hydroxymethyl-D,L-lysine (M+H=177) was eluted with 1 N NH₄OH.

EX-5C) The α-hydroxymethyl-D,L-lysine is protected as a copper complex via reaction with cupric carbonate in water at reflux.

EX-5) This protected amino acid is then reacted with chloroacetaldoxime as described in Example 1. The product is eluted from Dowex with 1N ammonium hydroxide. Concentration in vacuo, followed by acidification with hydrochloric acid affords the title compound.

EXAMPLE 6

N⁶-[1-(hydroxyimino)-2,2,2-trifluoroethyl]-L-lysine, dihydrochloride

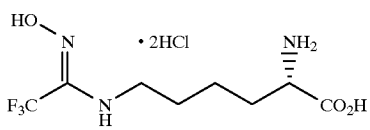

α-Boc-L-lysine is reacted with chlorotrifluoroacetaldoxime (J. Org. Chem. 49, (1984) 919–922) as described in Example 1 to afford the title compound.

EXAMPLE 7

N⁶-[1-(hydroxyimino)ethyl]-L-lysine, ethyl ester, dihydrochloride

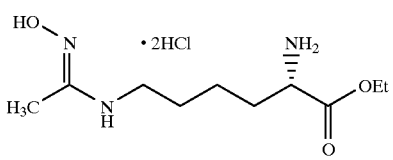

EX-7A) To a 125 mL flask is added 0.012 mol of α-Boc-L-lysine ethyl ester hydrochloride and 70 mL of water. This solution is adjusted to pH=8.5 by addition of 2.5 N NaOH. To this solution is added portion wise, 2.3 g of chloroacetaldoxime which is prepared immediately prior to use by the reaction of 3.55 g (0.06 mol) of acetaldoxime with 10.4 g (0.78 mol) of N-chlorosuccinimide in 65 mL of N,N-dimethylformamide at 0° C. The chloroacetaldoxime is isolated after three hours by extracting into diethyl ether and washing with aqueous NaCl. Drying with MgSO₄, filtering and concentrating under 30° C. affords the chloroacetaldoxime as a pale yellow oil. During the chloroacetaldoxime addition, the pH is kept at 8.5 via concomitant addition of 2.5 N NaOH. After the addition is complete, the solution is allowed to stand at 25° C. for 25 minutes. The solution is then adjusted to pH=7.5 with 1N HCl and poured onto a Dowex 50 Cation exchange column. The column is washed with water. The Boc-protected product is then eluted with 10% aqueous pyridine.

7a

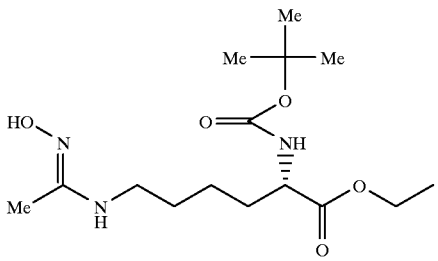

EX-7) After concentrating, the product is deprotected by allowing it to stand in 4N HCl in ethanol at 25° C. for twelve hours. Concentrating in vacuo at 30° C. affords L-N⁶-(hydroximinoethyl)lysine ethyl ester dihydrochloride.

EXAMPLE 8

N⁶-[1-(hydroxyimino)ethyl]-L-lysine, 2,3-dihydroxypropyl ester, dihydrochloride

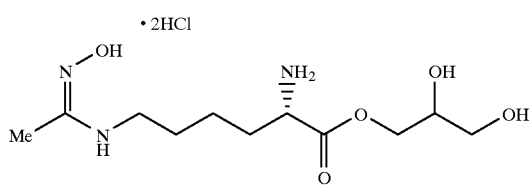

EX-8A) ε-Z-α-Boc-L-Lysine is reacted with DL-isopropylideneglycerol (Aldrich Chemical Co., Milwaukee, Wis., U.S.A.) in DMF in the presence of 1-hydroxybenzotriazole hydrate and [(N,N-dimethylamino)propyl]ethylcarbodiimide hydrochloride as described in 23c to give 8a.

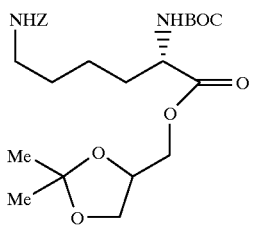

8a

EX-8B) The benzyloxycarbonyl (Z) group of 8a is removed with hydrogenolysis using 5% Pd/C in ethanol and the resulting deprotected amine is reacted with chloroacetaldoxime as described in the preparation of 7a to give 8b.

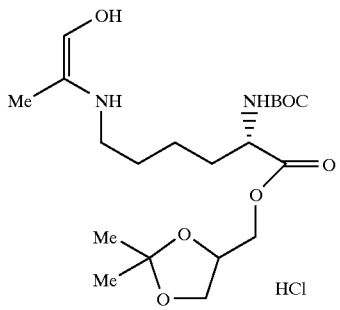

8b

EX-8) 8b is treated with 6M HCl in anhydrous ethanol overnight, evaporated to a solid, and triturated with ether to give the title compound 8.

EXAMPLE 9
$N^6$-[1-(hydroxyimino)ethyl]-L-lysine, 2-hydroxy-1-(hydroxymethyl)ethyl ester, dihydrochloride

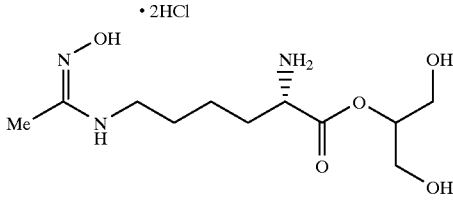

EX-9A) The process of Example 8 is repeated, with 1,3-benzylideneglycerol (H. Hibbert, N. M. Carter, J. Am. Chem. Soc., 1929, 51, 1601) replacing DL-isopropylideneglycerol.

EX-9B) After the chloroacetaldoxime step, the benzylidene group is removed with triethyl borate/boric acid as described in J. Med. Chem. 1980, ,23, 9–12 (G. Y. Paris et al). The reaction product is purified by reverse phase column chromatography.

EX-9) The title compound is procured after HCl/EtOH treatment as described in Example 8.

EXAMPLE 10
$N^6$-[1-(hydroxyimino)ethyl]-L-lysine, 2-(diethylamino)-2-oxoethyl ester, dihydrochloride

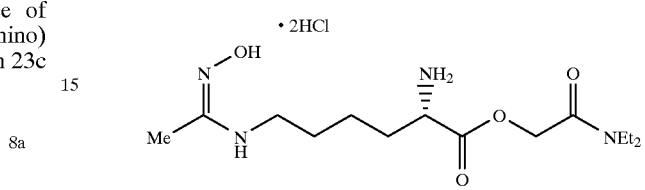

EX-10A) ε-Boc-α-Z-L-Lysine is reacted with 2-chloro-N,N-diethylacetamide (Aldrich Chemical Co.) in the presence of triethylamine and sodium iodide by the method described in Internat. J. Pharmaceutics, 1990, 62, 193–205 (A. H. Kahns and H. Bundgaard) to give 10a.

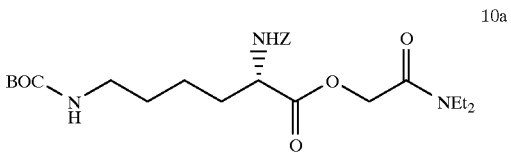

10a

EX-10) 10a is treated sequentially with HCl 4M in glacial acetic acid for three hours and then stripped to remove the Boc group, then chloroacetaldoxime as described in Example 7, and then hydrogenolyzed with 5% Pd/C in ethanol containing excess HCl and filtered and stripped to give the title compound.

EXAMPLE 11
S-ethyl 2S-amino-6-[[1(hydroxyimino)ethyl]amino]hexanethioate, dihydrochloride

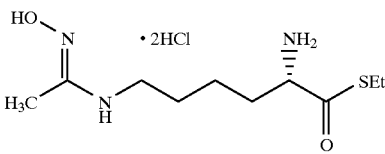

EX-11a) To a flask containing N-α-Boc-N-ε-Z-L-lysine in a suitable solvent is added an amino acid activating agent. This transient intermediate is then reacted with ethanethiol to produce the protected thioester.

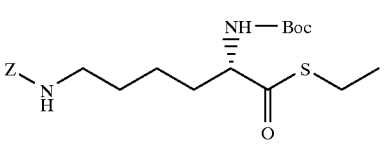

11a

EX-11B) The product of EXAMPLE 11a dissolved in an appropriate solvent is combined with a hydrogenation catalyst such as palladium on carbon and hydrogen. This reaction is shaken under pressure for an extended period of time in a standard Parr hydrogenation apparatus to remove the Z-function generating the amino product illustrated below.

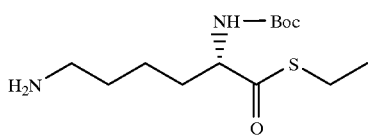
11b

EX-11C) The product of EXAMPLE 11b dissolved in an appropriate solvent is reacted with the chloroacetaldoxime whose synthesis is described in EXAMPLE 1 to yield the hydroxyimino material illustrated below.

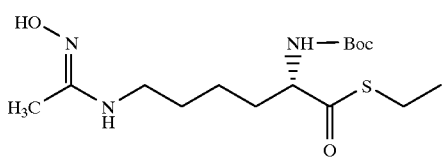
11c

EX-11) The product of EXAMPLE 11c dissolved in an appropriate solvent is reacted with HCl to remove the Boc-protecting group and provide the title compound.

EXAMPLE 12

$N^2$-[(acetyloxy)methyl]-$N^6$-[1-(hydroxyimino)ethyl]-L-lysine, dihydrochloride

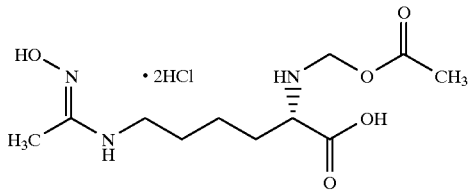

EX-12A) To a flask containing N-a-Boc-N-e-Z-L-lysine in a suitable solvent is added an amino acid activating agent. This transient intermediate is then reacted with benzylalcohol to produce the protected benzylester product illustrated below.

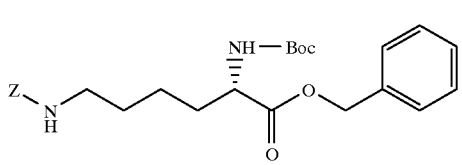
12a

EX-12B) The product of EXAMPLE 12a dissolved in an appropriate solvent is reacted with HCl to remove the Boc-protecting group and provide the product illustrated below.

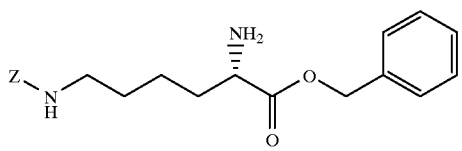
12b

EX-12C) The product of EXAMPLE 12b dissolved in an appropriate solvent is reacted with formaldehyde, $Cs_2CO_3$, and acetic anhydride to provide the product illustrated below.

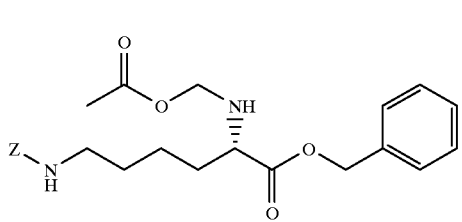
12c

EX-12D) The product of example 12c is dissolved in an appropriate solvent and combined with a hydrogenation catalyst such as palladium on carbon and hydrogen. This reaction is shaken under pressure for an extended period of time in a standard Parr hydrogenation apparatus to remove the Z-function generating the amino product illustrated below.

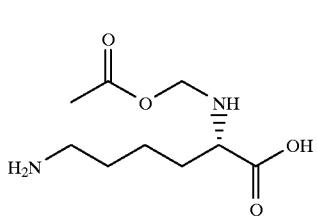
12d

EX-12) The product of EXAMPLE 12d dissolved in an appropriate solvent is reacted with the chloroacetaldoxime whose synthesis is described in EXAMPLE 1 to yield the hydroxyimino title material.

EXAMPLE 13

$N^6$-[1-(hydroxyimino)ethyl]-$N^2$-[[[(methylamino)carbonyl]oxy]methyl]-L-lysine, dihydrochloride

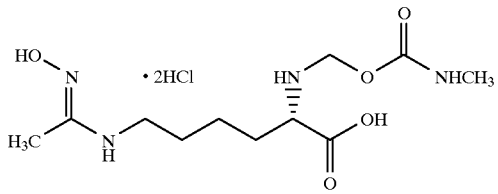

EXAMPLE 14

$N^6$-[1-(hydroxyimino)ethyl]-$N^2$-[[(methoxycarbonyl)oxy]methyl]-L-lysine, dihydrochloride

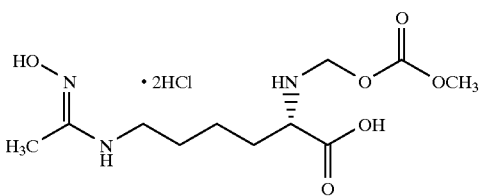

EXAMPLE 15
N⁶-[1-(hydroxyimino)ethyl]-N²-[[[(methylthio)carbonyl]oxy]methyl]-L-lysine, dihydrochloride

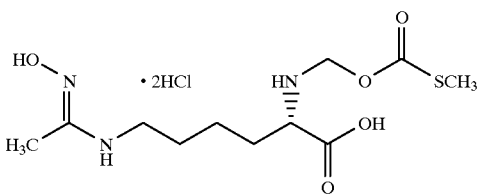

EXAMPLE 16
N⁶-[1-(hydroxyimino)ethyl]-N²-[[(phenylcarbonyl)oxy]methyl]-L-lysine, dihydrochloride

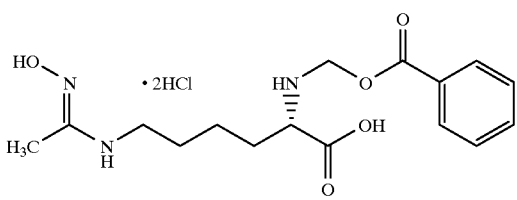

EXAMPLE 17
N²-acetyl-N²-[(acetyloxy)methyl]-N⁶-[1-(hydroxyimino)ethyl]-L-lysine, hydrochloride

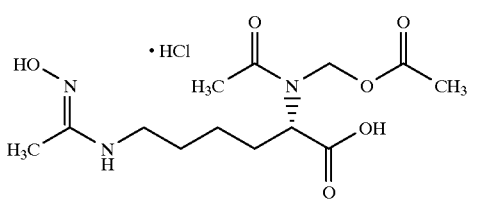

EX-17A) The product of EXAMPLE 12b dissolved in an appropriate solvent is reacted with $Cs_2CO_3$, and acetic anhydride to provide the product illustrated below.

17a

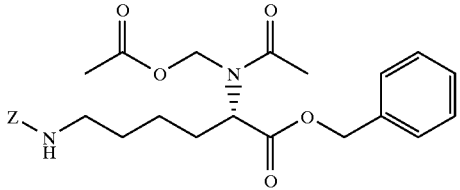

EX-17B) The product of EXAMPLE 17a dissolved in an appropriate solvent is combined with a hydrogenation catalyst such as palladium on carbon and hydrogen. This reaction is shaken under pressure for an extended period of time in a standard Parr hydrogenation apparatus to remove the Z-function generating the amino product illustrated below.

17b

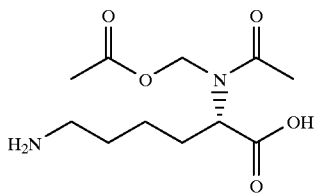

EX-17) The product of EXAMPLE 17b dissolved in an appropriate solvent is reacted with the chloroacetaldoxime whose synthesis is described in EXAMPLE 1 to yield the hydroxyimino title material.

EXAMPLE 18
N⁶-[1-(hydroxyimino)ethyl]-N²-[(methylthio)carbonyl]-L-lysine, hydrochloride

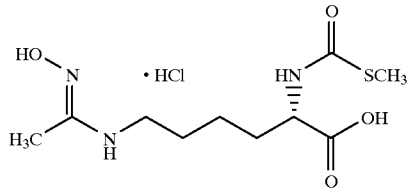

EXAMPLE 19
N²-[(1,1-dimethylethoxy)carbonyl]-N⁶-[1-(hydroxyimino)ethyl]-L-lysine, hydrochloride

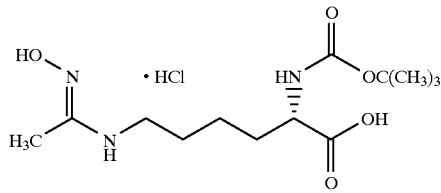

To a 125 mL flask was added 3 g (0.012 mol) of a-Boc-L-lysine and 70 mL of water. This solution was adjusted to pH=9.5 by addition of 2.5 N NaOH. To this solution was added portion wise, 2.3 g of chloroacetaldoxime which was prepared immediately prior to use by the reaction of 3.55 g (0.06 mol) of acetaldoxime with 10.4 g (0.78 mol) of N-chlorosuccinimide in 65 mL of N,N-dimethylformamide at 0° C. The chloroacetaldoxime was isolated after three hours by extracting into diethyl ether and washing with aqueous NaCl. Drying with $MgSO_4$, filtration and concentration under 30° C. afforded the chloroacetaldoxime as a pale yellow oil. During the chloroacetaldoxime addition, the pH was kept at 9.5 via concomitant addition of 2.5 N NaOH. After the addition was complete, the solution was allowed to stand at 25° C. for 25 minutes. The solution was then adjusted to pH=7.5 with 1N HCl and poured onto a Dowex 50 Cation exchange column. The column was washed with water. The Boc-protected product was then eluted with 10% aqueous pyridine. $^1$H-NMR($D_2O$) 1.25 (s, 9 H); 1.4–1.65 (m, 6 H), 2.05 (s, 3 H), 3.22 (t, 2 H), 3.75 (m, 1 H); Mass Spectra, M+H=304.

EXAMPLE 20

$N^6$-[1-(hydroxyimino)ethyl]-$N^2$-[(methylamino)carbonyl]-L-lysine, hydrochloride

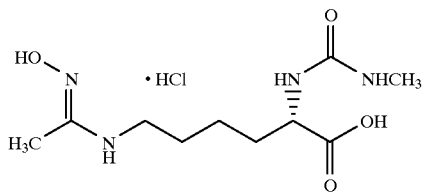

EX-20A) Epsilon-Boc-lysine is allowed to react with methyl isocyanate to afford the urea.

20a

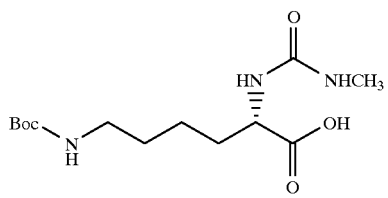

EX-20B) Deprotection with HCl removes the Boc to afford the amine.

20b

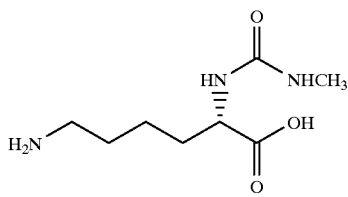

EX-20) Reaction with acetaldoximinoyl chloride as in example 1 affords the title product.

EXAMPLE 21

$N^6$-[1-(hydroxyimino)ethyl]-$N^2$-[$N^6$-[1-(hydroxyimino)ethyl]-L-lysyl]-L-lysine, ethyl ester, trihydrochloride

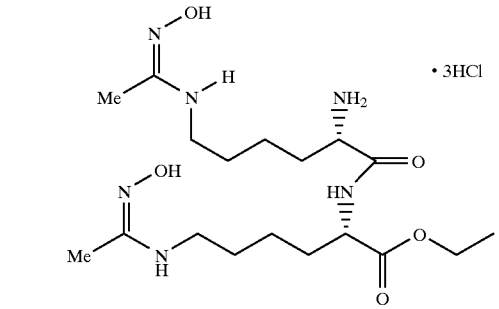

EX-21A) ε-Boc-L-Lys(Z)-OH (3.8 g, 10 mmol) in 25 mL DMF and 25 mL dichloromethane (DCM) is reacted with isobutyl chloroformate (1.4 mL, (10 mmol) in the presence of NMM (1.1 mL, 10 mmol). The resulting mixed anhydride is reacted with 10 mmol α-Boc-L-Lys-OEt HCl salt suspended in 25 mL DMF containing 10 mmol NMM. After mixing for 16 hr, the reaction mixture is filtered, the residue washed with DCM (25 mL), and the combined filtrate and wash is extracted by 0.5 M KHSO$_4$ solution, followed by water extraction, and then brine extraction. The organic phase is dried (MgSO$_4$), filtered, and stripped to an oil. The oil is purified by silica gel chromatography if necessary, giving 21a.

21a

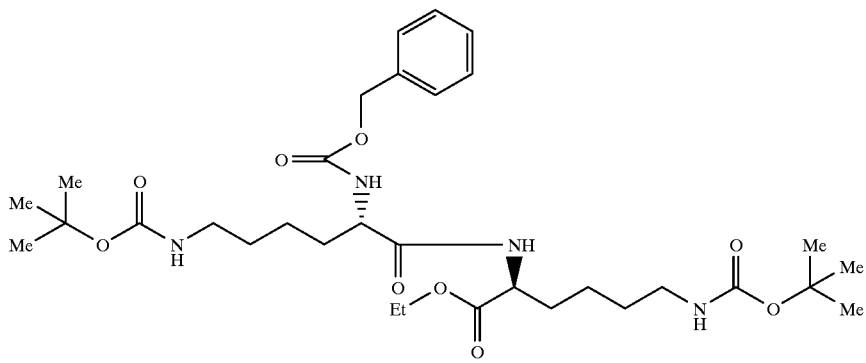

EX-21B) 21a is treated with 4 M HCl in ethanol overnight at room temperature. The reaction mixture is stripped to a solid, giving 21b.

21b

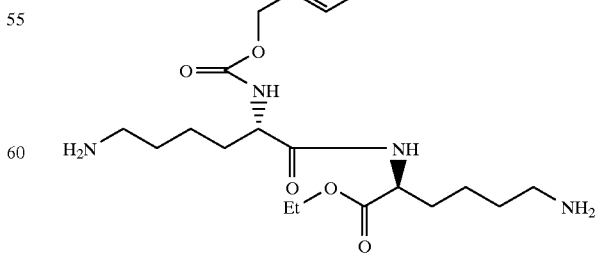

EX-21C) 21b is dissolved in water, and the pH is adjusted to 8.5 with 2.5 N NaOH. This solution is treated with a fivefold excess of chloroacetaldoxime as described in example 7, through the elution with aqueous pyridine. The product is stripped to an oil, giving 21c.

diisopropylethylamine (1.05 mL, 6 mmol) overnight. Solvent is removed in vacuo and the residue is purified by reverse phase column chromatography, giving 23a.

21c

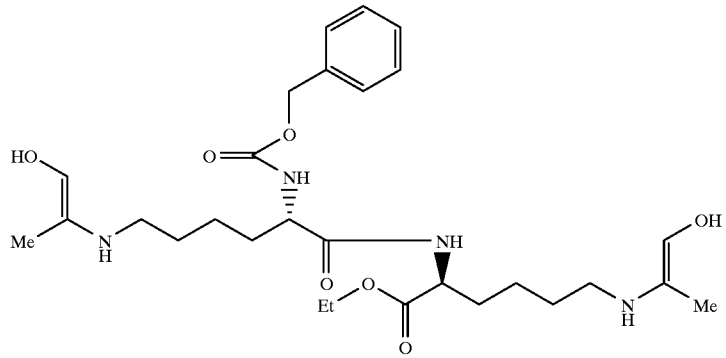

EX-21) 21c is hydrogenolyzed ($H_2$ 10 psi) with 5% Pd/C in ethanol containing an excess of HCl. The title compound 21 is isolated by stripping the solution to a solid, and triturating this solid with ether.

EXAMPLE 22
$N^6$-[1-(hydroxyimino)ethyl]-$N^2$-[$N^6$-[1-(hydroxyimino)ethyl]-L-lysyl]-L-lysine, trihydrochloride

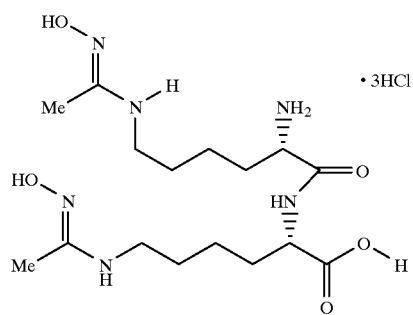

The procedure of Example 21 is repeated, with the HCl salt of ε-Boc-L-Lys benzyl ester (εBoc-L-Lys-OBz HCl) replacing the ε-Boc-L-Lys-OEt HCl salt. The final hydrogenolysis then gives the title compound.

EXAMPLE 23
$N^6$-[1-(hydroxyimino)ethyl]-$N^2$-[$N^6$-(1-iminoethyl)-L-lysyl]-L-lysine, ethyl ester, trihydrochloride

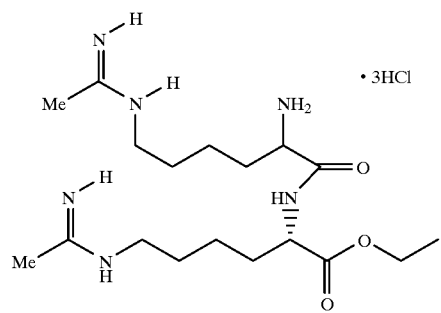

EX-23A) α-Z-L-Lysine ethyl ester in 10 mL DMF is treated with methyl acetimidate (0.692 g, 6 mmol) and N,N-

23a

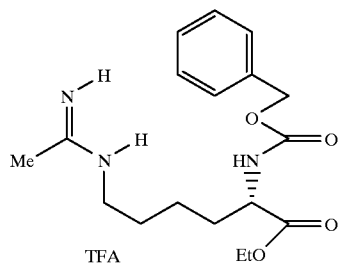

EX-23B) The product $N^6$-[1-iminoethyl]-L-Lys(Z)-OEt trifluoroacetate (TFA) salt (23a) is treated with refluxing aqueous 6M HCl overnight and stripped to give $N^6$-[1-iminoethyl]-L-Lys(Z)-OH HCl salt (BP4b). Passage through an anion exchange column in the chloride form can be used if necessary to fully replace the TFA.

23b

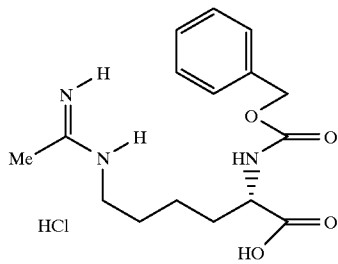

EX-23C) To a stirring solution of $N^6$-[1-iminoethyl]-L-Lys(Z)-OH HCl salt (23b, 13.8 mmol), ε-Boc-L-Lys-OEt (39.5 mmol), and 1-hydroxybenzotriazole hydrate (2 g, 14.5 mmol) in 75 mL of dimethylformamide (DMF) cooled in an ice bath is added [(N,N-dimethylamino)propyl]ethylcarbodiimide hydrochloride (2.8 g, 14.5 mmol). After stirring 55 h at ambient temperature, the reaction mixture is concentrated in vacuum. The resulting material is dissolved in aqueous acetonitrile and passed through a reverse phase chromatographic column, giving α-(Z)-ε-N-iminoethyl-L-Lysyl-ε-Boc-L-Lysine ethyl ester TFA salt (23c).

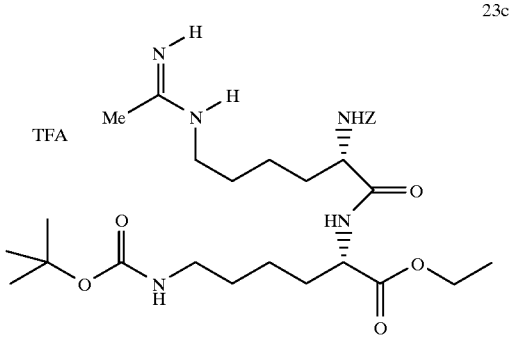

EX-23) This material is treated with ethanolic HCl as described for 21b, dissolved in water and treated with chloroacetaldoxime, followed by hydrogenolysis, both as described in Example 21, to give the title compound 23.

EXAMPLE 24
$N^6$-[1-(hydroxyimino)ethyl]-$N^2$-[$N^6$-(1-iminoethyl)-L-lysyl]-L-lysine, trihydrochloride

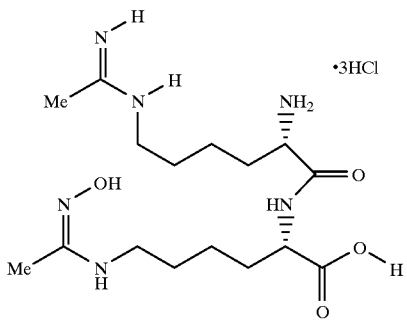

The procedure of Example 23 is carried out, with α-Boc-L-Lys-OBz replacing ε-Boc-L-Lys-OEt, to give the title compound.

EXAMPLE 25
$N^2$-(N-acetyl-L-methionyl)-$N^6$-[1-(hydroxyimino)ethyl]-L-lysine, ethyl ester, hydrochloride

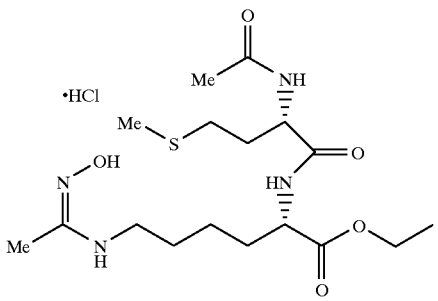

The procedure of Example 21 is run through the elution with aqueous pyridine, with N-acetyl-L-methionine replacing ε-Boc-L-Lys(Z)-OH. The aqueous pyridine solution is stripped to a solid, dissolved in dilute HCl, and shelled and lyophilized to give title compound.

EXAMPLE 26
$N^2$-(N-acetylmethionyl)-$N^6$-[1-(hydroxyimino)ethyl]-L-lysine, hydrochloride

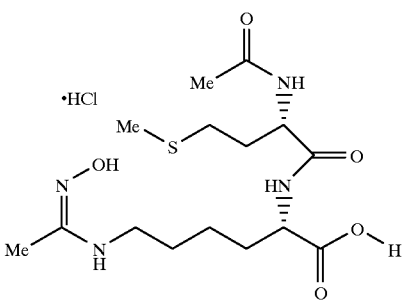

The title compound of Example 25 is treated with refluxing aqueous 6N HCl for 12 hr and then stripped to a solid to give the title compound.

EXAMPLE 27
$N^2$-(L-alanyl)-$N^6$-[1-(hydroxyimino)ethyl]-L-lysine, dihydrochloride

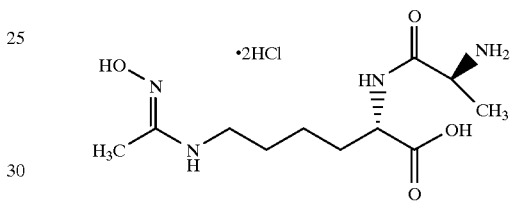

EX-27A) The product of example 1 is dissolved in ethanol, cooled down in ice bath and HCl gas is bubbled into the solution. This solution is stirred at room temperature followed by removal of the solvent in vacuo to obtain the ethyl ester.

EX-27B) This ester is coupled with $N^\alpha$-Boc-L-alanine in dimethylformamide (DMF) in the presence of [2-(1H-benzotriazol-1-yl)-1,1,3,3-tetramethyluronium tetrafluoroborate] (TBTU) and diisopropylethylamine (DIPEA). The solvent is removed in vacuo and the product is isolated on preparative HPLC using acetonitrile/$H_2O$ gradient.

EX-27) Protecting groups are removed in 2N HCl at reflux. The title compound is isolated on preparative HPLC using acetonitrile/$H_2O$ gradient.

EXAMPLE 28
$N^6$-[1-[[(methoxycarbonyl)oxy]imino]ethyl]-L-lysine, dihydrochloride

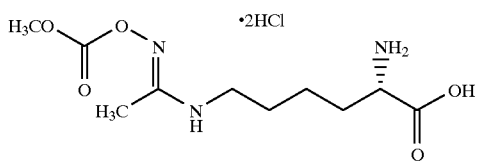

EXAMPLE 29
$N^6$-[1-[[[(methylamino)carbonyl]oxy]imino]ethyl]-L-lysine, dihydrochloride

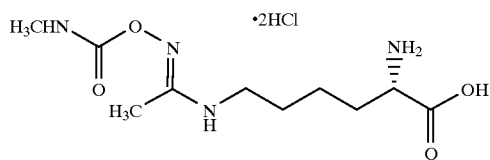

EXAMPLE 30
$N^6$-[1-[[[(methylthio)carbonyl]oxy]imino]ethyl]-L-lysine, dihydrochloride

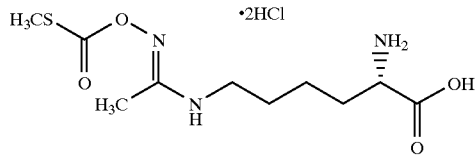

EXAMPLE 31
$N^6$-[1-[(acetyloxy)imino]ethyl]-L-lysine, dihydrochloride

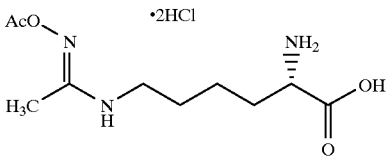

EX-31A) To N-alpha-boc-L-lysine (Aldrich) in water at pH 9, is added O-acetyl-2-chloroacetaldehyde oxime, adjusting to pH 9 throughout the reaction with 2.5N sodium hydroxide. Contents are purified on a Dowex-50 cation exchange resin, eluting the boc-protected product with 1N ammonium hydroxide.

EX-31) Acidic hydrolysis and purification by C18 reverse phase chromatography affords the desired product.

EXAMPLE 32
$N^6$-[1-[[(phenylcarbonyl)oxy]imino]ethyl]-L-lysine, dihydrochloride

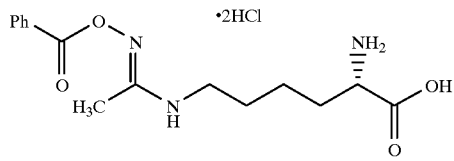

EXAMPLE 33
N6-[1-[(methoxyimino)ethyl]-L-lysine, dihydrochloride

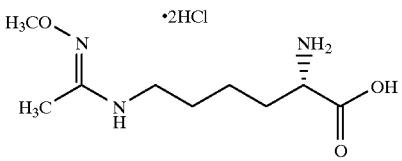

EX-33A) To N-alpha-boc-L-lysine (Aldrich) in water at pH 9, is added O-methyl-2-chloroacetaldehyde oxime, adjusting to pH 9 throughout the reaction with 2.5N sodium hydroxide. Contents are purified on a Dowex-50 cation exchange resin, eluting the boc-protected product with 1N ammonium hydroxide.

EX-33) Acidic hydrolysis and purification by C18 reverse phase chromatography affords the desired product.

EXAMPLE 34
$N^6$-[1-[(phenoxyimino)ethyl]-L-lysine, dihydrochloride

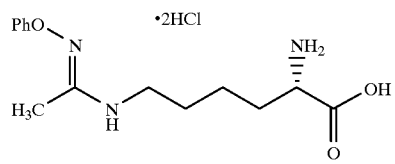

EXAMPLE 35
$N^6$-hydroxy-$N^6$-[1-(hydroxyimino)ethyl]-L-lysine, dihydrochloride

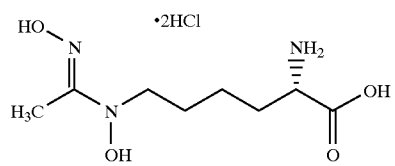

EXAMPLE 36
$N^6$-[1-(hydroxyimino)ethyl]-$N^6$-[[[(methoxycarbonyl)oxy]methyl]-L-lysine, dihydrochloride

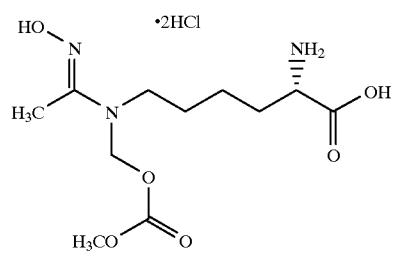

EXAMPLE 37
$N^6$-[1-(hydroxyimino)ethyl]-$N^6$-[[[(methylamino)carbonyl]oxy]methyl]-L-lysine, dihydrochloride

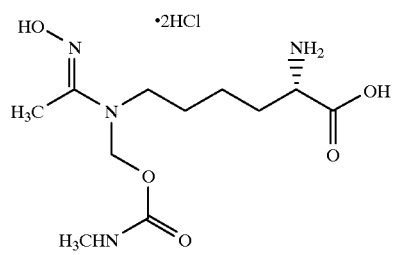

EXAMPLE 38
$N^6$-[1-(hydroxyimino)ethyl]-$N^6$-[[[(methylthio)carbonyl]oxy]methyl]-L-lysine, dihydrochloride

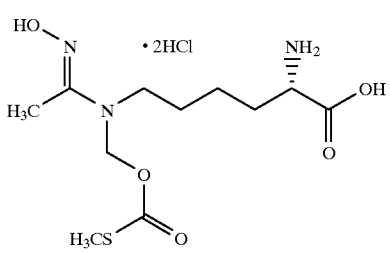

EXAMPLE 39
$N^6$-[1-(hydroxyimino)ethyl]-$N^6$-[[(phenylcarbonyl)oxy]methyl]-L-lysine, dihydrochloride

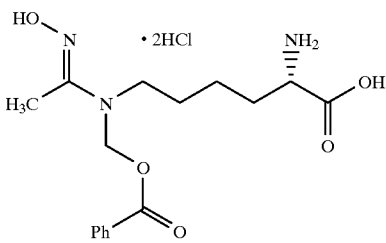

EXAMPLE 40
N6-(acetyloxy)-N6-(1-iminoethyl)-L-lysine, dihydrochloride

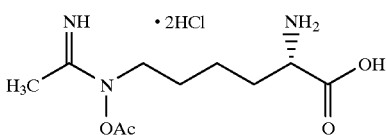

EX-40A) α-Cbz-protected hydroxylysine methyl ester is prepared as described in J. Org. Chem. 59, 4858–4861 (1994). This material is then allowed to react with ethyl acetimidate to afford the hydroxamidine.

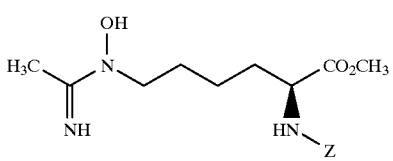

40a

EX-40B) Reaction with acetic anhydride affords the acetyl-hydroxamidine.

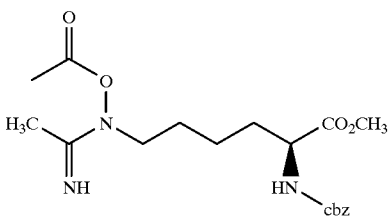

40b

EX-40) Deprotection with HBr in acetic acid affords the title compound.

EXAMPLE 41
$N^6$-[1-[(phenylthio)imino]ethyl]-L-lysine, dihydrochloride

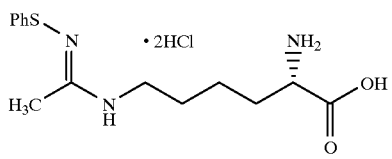

EXAMPLE 42
$N^6$-(1-iminoethyl)-$N^6$-(phenylmethoxy)-L-lysine, dihydrochloride

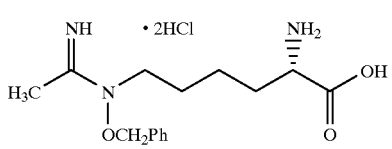

EX-42A) Omega benzyloxy acetyllysine methyl ester is prepared as described in Tet. Let. 25(9), 927–930 (1994). This material is hydrolyzed to afford benzyloxylysine.

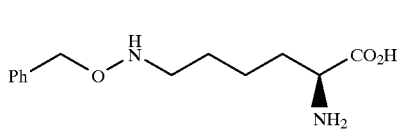

42a

EX-42) Protection of the amino acid with $Cu^{2+}$ allows reaction with ethyl acetimidate in basic water. Purification via Dowex 50 ion exchange resin affords the title compound.

EXAMPLE 43
$N^6$-hydroxy-$N^6$-(1-iminoethyl)-L-lysine, dihydrochloride

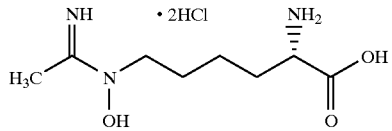

EXAMPLE 44
N6-acetyloxy-N6-[1-[(acetyloxy)imino]ethyl]-L-lysine, dihydrochloride

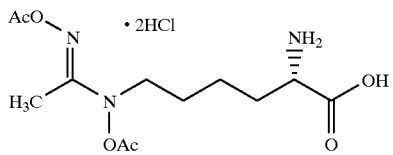

EX-44A) α-Cbz-protected hydroxylysine methyl ester is prepared as described in J. Org. Chem. 59, 4858–4861 (1994). This material is then allowed to react with acetaldoximinoyl chloride to afford the N, N' dihydroxyamidine.

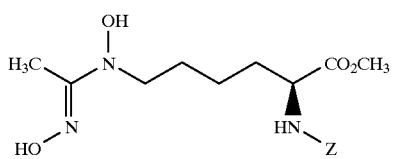

44a

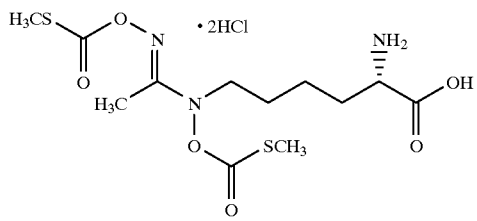

EX-44B) Reaction with acetic anhydride affords the bis-acetoxyamidine.

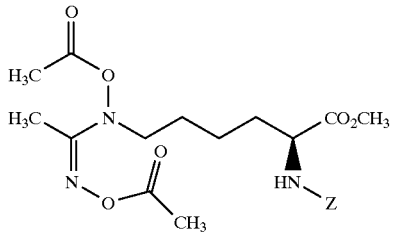

44b

EX-44) Deprotection with HBr in acetic acid affords the title compound.

EXAMPLE 45

$N^6$-[1-[[(methoxycarbonyl)oxy]imino]ethyl]-$N^6$-[(methoxycarbonyl)oxy]-L-lysine, dihydrochloride

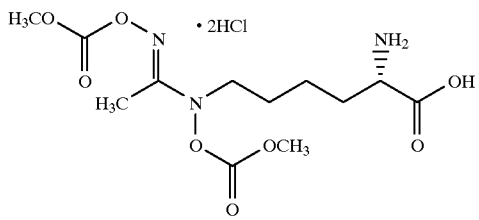

EXAMPLE 46

$N^6$-[1-[[[(methylamino)carbonyl]oxy]imino]ethyl]-$N^6$-[[(methylamino)carbonyl]oxy]-L-lysine, dihydrochloride

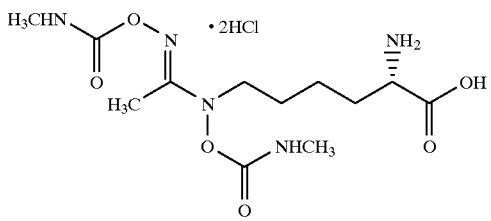

EXAMPLE 47

N6-[1-[[[(methylthio)carbonyl]oxy]imino]ethyl]-N6-[[(methylthio)carbonyl]oxy]-L-lysine, dihydrochloride

EXAMPLE 48

$N^6$-[1-[[(phenylcarbonyl)oxy]imino]ethyl]-$N^6$-[(phenylcarbonyl)oxy]-L-lysine, dihydrochloride

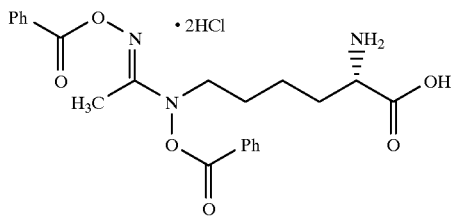

EXAMPLE 49

$N^6$-[1-(phenoxyimino)ethyl]-$N^6$-phenoxy-L-lysine, dihydrochloride

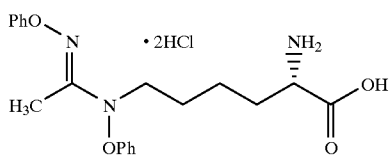

EXAMPLE 50

$N^6$-[1-(methoxyimino)ethyl]-$N^6$-(phenylmethoxy)-L-lysine, dihydrochloride

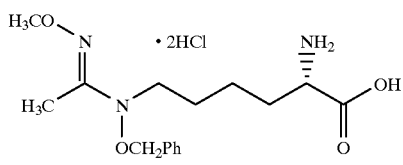

EX-50A) Omega benzyloxy acetyllysine methyl ester is prepared as described in Tet. Let. 25(9), 927–930 (1994). This material is hydrolyzed to afford benzyloxylysine.

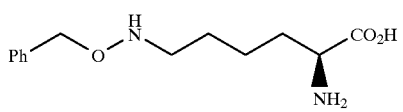

50a

EX-50) Protection of the amino acid with $Cu^{2+}$ allows reaction with O-methyl acetoximinoyl chloride in basic water. Purification via Dowex 50 ion exchange resin affords the title compound.

EXAMPLE 51

$N^6$-[1-[[(acetyloxy)methyl]imino]ethyl]-$N^6$-hydroxy-L-lysine, dihydrochloride

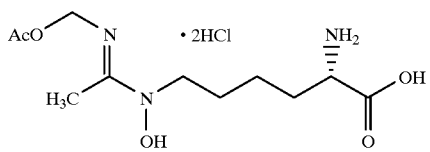

EX-51A) α-Cbz-protected hydroxylysine methyl ester is prepared as described in J. Org. Chem. 59, 4858–4861 (1994). This material is then allowed to react with $CH_3C(OEt)=NCH_2OAc$ to afford the hydroxamidine.

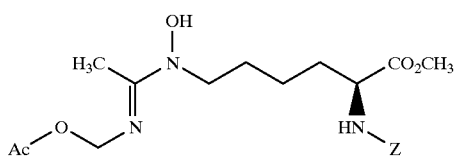

51a

EX-51) Deprotection with HBr in acetic acid affords the title compound.

EXAMPLE 52
$N^6$-hydroxy-$N^6$-[1-[[[(methoxycarbonyl)oxy]methyl]imino]ethyl]-L-lysine, dihydrochloride

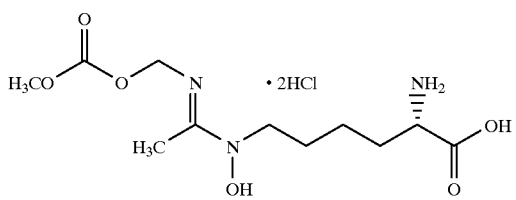

EXAMPLE 53
$N^6$-hydroxy-$N^6$-[1-[[[[(methylamino)carbonyl]oxy]methyl]imino]ethyl]-L-lysine, dihydrochloride

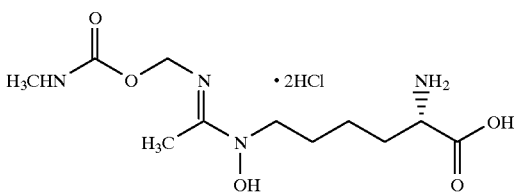

EXAMPLE 54
$N^6$-hydroxy-$N^6$- [1-[[[[(methylthio)carbonyl]oxy]methyl]imino]ethyl]-L-lysine, dihydrochloride

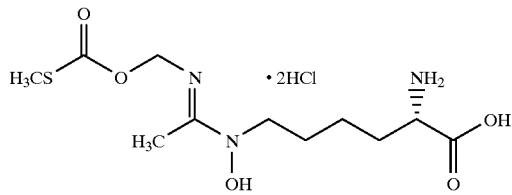

EXAMPLE 55
$N^6$-hydroxy-$N^6$-[1-[[[(phenylcarbonyl) oxy]methyl]imino]ethyl]-L-lysine, dihydrochloride

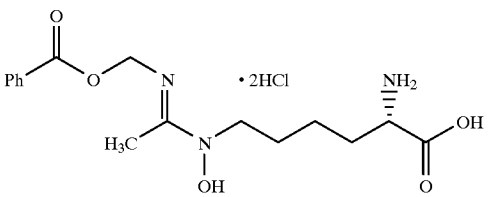

EXAMPLE 56
$N^6$-[(acetyloxy)methyl]-$N^6$-[1-(hydroxyimino)ethyl]-L-lysine, dihydrochloride

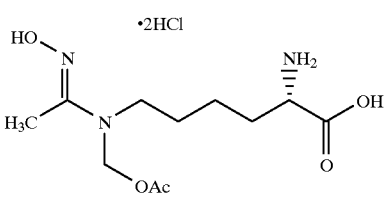

EX-56A) α-Fmoc, ε-Cbz-lysine is allowed to react with formaldehyde followed by acetic anhydride.

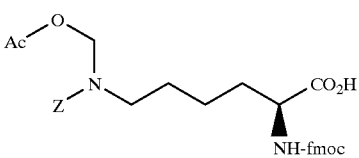

56a

EX-56B) Deprotection of the Cbz via catalytic hydrogenation affords the acetoxymethyl lysine.

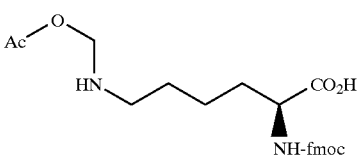

56b

EX-56) Reaction of this material with acetaldoximinoyl chloride followed by Fmoc deprotection affords the title compound.

EXAMPLE 57
$N^6$-(1-iminoethyl)-$N^6$-[(methoxycarbonyl)oxy]-L-lysine, dihydrochloride

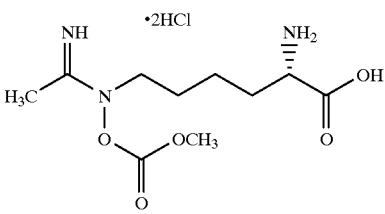

EXAMPLE 58
$N^6$-(1-iminoethyl)-$N^6$-[[(methylamino)carbonyl]oxy]-L-lysine, dihydrochloride

EXAMPLE 59
N⁶-(1-iminoethyl)-N⁶-[[(methylthio)carbonyl]oxy]-L-lysine, dihydrochloride

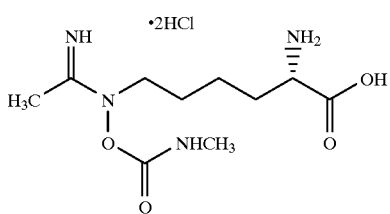

EXAMPLE 60
N⁶-(1-iminoethyl)-N⁶-[(phenylcarbonyl)oxy]-L-lysine, dihydrochloride

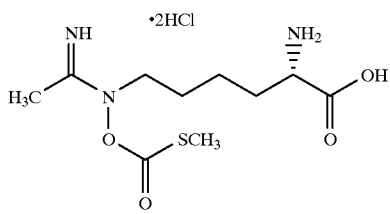

EXAMPLE 61
N⁶-(1-iminoethyl)-N⁶-phenoxy-L-lysine, dihydrochloride

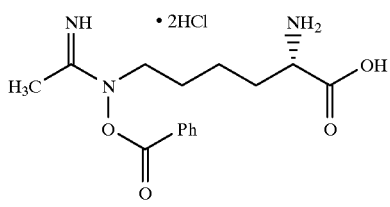

EXAMPLE 62
N⁶-[1-[(methylthio)imino]ethyl]-L-lysine, dihydrochloride

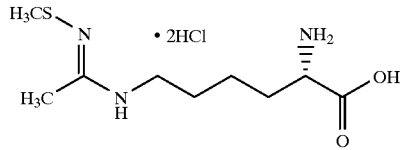

EX-62A) To a flask is added N-α-Boc-L-lysine methyl ester hydrochloride and water. This solution is adjusted to pH=8.5 by addition of 2.5 N NaOH. To this solution is added portion wise, methylacetimidate hydochloride. During the methylacetimidate hydochloride addition, the pH is kept at 8.5 to 10 via concomitant addition of 2.5 N NaOH. After the addition is complete, the solution is allowed to stand at 25° C. for 25 minutes. The solution is then adjusted to pH=7.5 with 1N HCl and poured onto a Dowex 50 Cation exchange column. The column is washed with water. The Boc-protected product is then eluted with 10% aqueous pyridine.

EX-62B) To a flask is added the amidine free base in chloroform at −70° C. followed by the addition of methanesulfenylchloride. The solvent is concentrated under vacuum and the resulting material is triturated with ether. The resulting product is collected by filtration and recrystallized from alcohol.

EX-62) The product is then deprotected by allowing it to stand in 2N HCl in ethanol at 25° C. The product is isolated by reverse phase HPLC chromatography.

EXAMPLE 63
N6-(1-iminoethyl)-N6-(methylthio)-L-lysine, dihydrochloride

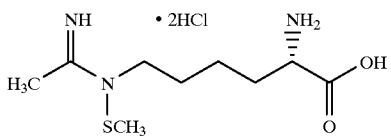

EX-63A) To a flask is added N-α-Boc-L-lysine methyl ester hydrochloride and water. This solution is adjusted to pH=8.5 by addition of 2.5 N NaOH. To this solution is added portion wise, methylacetimidate hydrochloride. During the methylacetimidate hydrochloride addition, the pH is kept at 8.5 to 10 via concomitant addition of 2.5 N NaOH. After the addition is complete, the solution is allowed to stand at 25° C. for 25 minutes. The solution is then adjusted to pH=7.5 with 1N HCl and poured onto a Dowex 50 Cation exchange column. The column is washed with water. The Boc-protected product is then eluted with 10% aqueous pyridine.

EX-63B) To a flask is added the amidine free base in chloroform at −70° C. followed by the addition of methanesulfenylchloride. The solvent is concentrated under vacuum and the resulting material is triturated with ether. The resulting product is collected by filtration and recrystallized from alcohol.

EX-63) The product is then deprotected by allowing it to stand in 2N HCl in ethanol at 25° C. The product is isolated by reverse phase HPLC chromatography.

EXAMPLE 64
N⁶-(1-iminoethyl)-N⁶-(phenylthio)-L-lysine, dihydrochloride

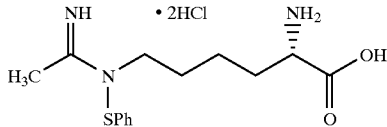

EXAMPLE 65
N⁶-[1-[(phenylthio)imino]ethyl]-L-lysine, dihydrochloride

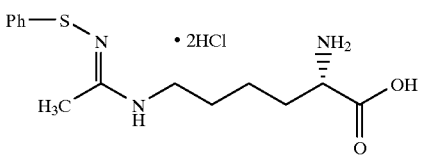

EXAMPLE 66
5-[4-[[1-(hydroxyimino)ethyl]amino]butyl]imidazolidine-2,4-dione, dihydrochloride

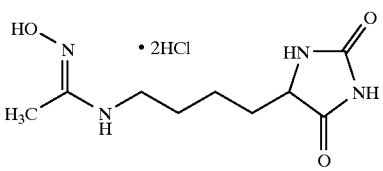

The title product of EXAMPLE 1 dissolved in water is reacted potassium cyanate in the presence of HCl as described in Bull. Soc. Chim. Fr. 1954, 812, 815 to provide the title material

EXAMPLE 67
N-[N⁶-[1-(hydroxyimino)ethyl]-L-lysyl]-L-alanine, dihydrochloride

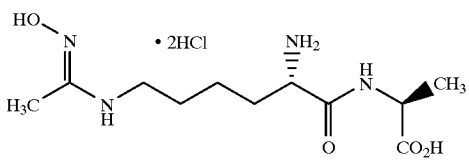

EXAMPLE 68
2S-amino-6-[[1-(hydroxyimino)ethyl]amino]-4-hexenoic acid, dihydrochloride

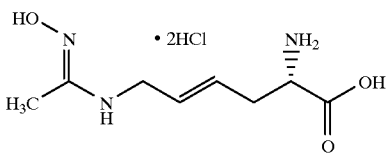

EXAMPLE 69
N-[2S-amino-2-[3-[[[1-(hydroxyimino)ethyl]amino]methyl]cyclopentyl]acetyl]-L-alanine, dihydrochloride

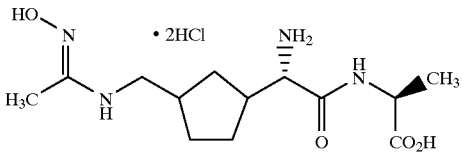

EXAMPLE 70
N-[2S-amino-2-[3-[[[1-(hydroxyimino)ethyl]amino]methyl]isoxazol-5-yl]acetyl]-L-alanine, dihydrochloride

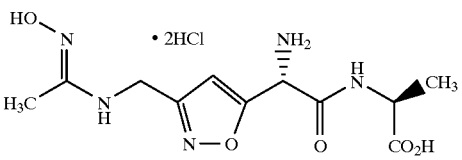

EXAMPLE 71
N²-(4-amino-1-oxobutyl)-N⁶-[1-(hydroxyimino)ethyl]-L-lysine, ethyl ester, dihydrochloride

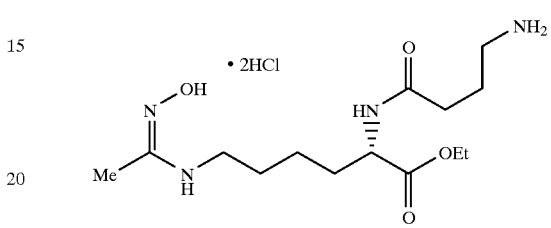

EX-71A) To a stirring solution of N-Boc-γ-aminobutyric acid (Sigma Chemical Co., St. Louis, Mo., U.S.A.), ε-Z-L-Lys-OEt, and 1-hydroxybenzotriazole hydrate in (DMF) cooled in an ice bath is added [(N,N-dimethylamino)propyl]ethylcarbodiimide hydrochloride as described in Example 23c. After stirring 55 h at ambient temperature, the reaction mixture is concentrated in vacuum to a semisolid, and partitioned between ethyl acetate and water. The organic phase is washed with water and then brine, dried (MgSO₄), filtered and stripped to give 71a.

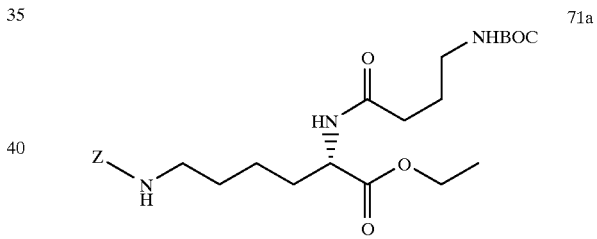

EX-71) 71a is treated sequentially with 5% Pd/C in ethanol and hydrogen at 10 psi, then chloroacetaldoxime as described in Example 7, and then HCl 4M in ethanol for thirteen hours and then stripped and triturated with ether to give the title compound.

EXAMPLE 72
N²-[[(2-aminoethyl)amino]carbonyl]-N⁶-[1-(hydroxyimino)ethyl]-L-lysine, ethyl ester, dihydrochloride

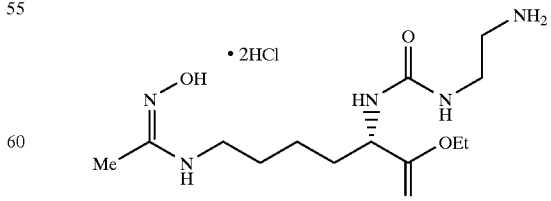

EX-72A) ε-Z-L-Lys-OEt is treated with stochiometric amounts of carbonyldiimidazole and imidazole, both from Aldrich Chemical Co., in THF, to give 72a.

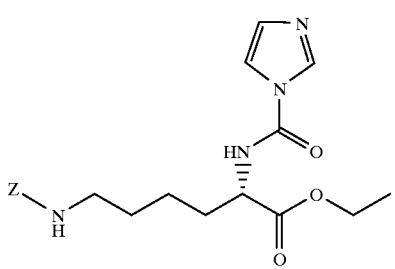
72a

EX-72B) After 12 hours at room temperature the product 72a is treated with an excess of t-butyl N-(2-aminoethyl) carbamate (N-Boc ethylene diamine, from Aldrich Chemical Co.) to give 72b.

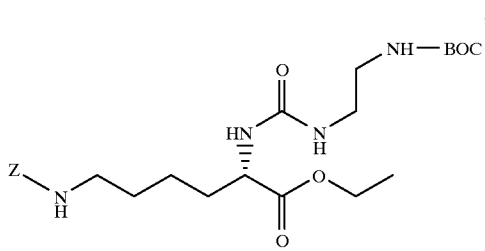
72b

EX-72) 72b is treated sequentially with 5% Pd/C in ethanol and hydrogen at 10 psi, then chloroacetaldoxime as described in Example 7, and then HCl 4M in ethanol for thirteen hours and then stripped and triturated with ether to give the title compound

EXAMPLE 73
$N^2$-[(2-aminoethoxy)carbonyl]-$N^6$-[1-(hydroxyimino) ethyl]-L-lysine, ethyl ester, dihydrochloride

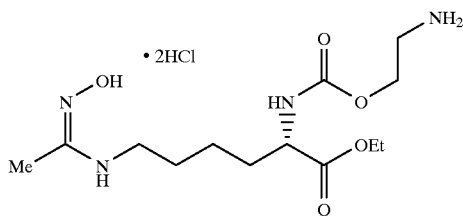

The process described in Example 72 is repeated, except that N-Boc-glycinol (Aldrich Chemical Co.) replaces t-butyl N-(2-aminoethyl)carbamate.

EXAMPLE 74
9S-amino-5,6,7,8,9,10-hexahydro-3-methyl-4H-1,2,4-oxadiazecin-10-one, dihydrochloride

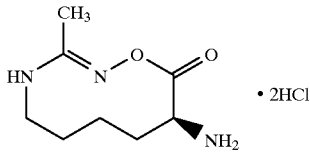

The product of example 7 is heated in a high boiling solvent to effect ethanol evolution. Removal of the solvent in vacuo followed by chromatographic purification affords the title compound.

EXAMPLE 75
3S-aminohexahydro-1-[1-(hydroxyimino)ethyl]-2H-azepin-2-one, dihydrochloride

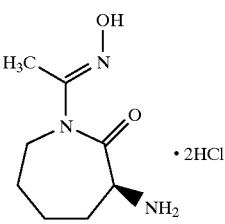

EX-75A) 3-aminocaprolactam is protected with Boc anhydride to give the bis-protected aminocaprolactam after chromatographic isolation.

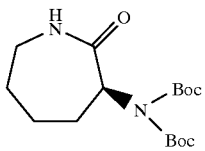
75a

EX-75B) Formation of the amide anion with a lithium amide base followed by reaction with acetaldoximinoyl chloride affords the hydroxamidine.

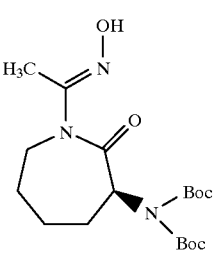
75b

EX-75) Deprotection with HCl affords the title product.

Biological Data

The subject compounds of formula (I) have been or are expected to be found to inhibit nitric oxide synthase and posses useful pharmacological properties as demonstrated in one or more of the following assays:

Citrulline Assay for Nitric Oxide Synthase

NOS activity was measured by monitoring the conversion of L-[2,3-$^3$H]-arginine to L-[2,3-$^3$H]-citrulline. Mouse inducible NOS (miNOS) was prepared from an extract of LPS-treated mouse RAW 264.7 cells and rat brain constitutive NOS (rnNOS) was prepared from an extract of rat cerebellum. Both preparations were partially purified by DEAE-Sepharose chromatography. Enzyme (10 μL) was added to 40 μL of 50 mM Tris (pH 7.6) and the reaction initiated by the addition of 50 μL of a solution containing 50 mM Tris (pH 7.6), 2.0 mg/mL bovine serum albumin, 2.0 mM DTT, 4.0 mM CaCl$_2$, 20 μM FAD, 100 &M tetrahydrobiopterin, 2.0 mM NADPH and 60 μM L-arginine containing 0.9 μCi of L-[2,3-$^3$H]-arginine. For constitutive NOS, calmodulin was included at a final concentration of 40 nM. Following incubation at 37° C. for 15 minutes, the reaction was terminated by addition of 300 μL cold buffer containing 10 mM EGTA, 100 mM HEPES (pH 5.5) and 1.0 mM L-citrulline. The [³H]-citrulline was separated by chromatography on Dowex 50W X-8 cation exchange resin and radioactivity quantified with a liquid scintillation counter.

Raw Cell Nitrite Assay

RAW 264.7 cells are plated to confluency on a 96-well tissue culture plate grown overnight (17 h) in the presence of LPS to induce NOS. A row of 3–6 wells were left untreated and served as controls for subtraction of nonspecific background. The media was removed from each well and the cells are washed twice with Kreb-Ringers-Hepes (25 mM, pH 7.4) with 2 mg/ml glucose. The cells are then placed on ice and incubated with 50 mL of buffer containing L-arginine (30 mM) +/- inhibitors for 1 h. The assay is initiated by warming the plate to 37%C in a water bath for 1 h. Production of nitrite by intracellular iNOS is linear with time. To terminate the cellular assay, the plate of cells is placed on ice and the nitrite-containing buffer removed and analyzed for nitrite using a previously published fluorescent determination for nitrite. T. P. Misko et al, *Analytical Biochemistry*, 214, 11–16 (1993). All values are the average of triplicate wells and are compared to a background-subtracted induced set of cells (100% value).

In Vivo Assay

Rats were treated with an intraperitoneal injection of 10 mg/kg of endotoxin (LPS) with or without oral administration of the nitric oxide synthase inhibitors. Plasma nitrites were measured 5 hours post-treatment. The results show that the administration of the nitric oxide synthase inhibitor decreases the rise in plasma nitrites, a reliable indicator of the production of nitric oxide, induced be endotoxin.

TABLE I

Rodent (Cell Data and in vitro Enzyme Data)

| Compound | miNOS* IC50 [μM] | rnNOS* | Raw Cell* IC50 [μm] |
|---|---|---|---|
| Example 1 | 77 | 1470 | 28 |

*miNOS refers to mouse inducible NOS
rnNOS refers to rat brain constitutive NOS
Raw Cell refers to cultured RAW 264.7 cells

TABLE II

Human (in vitro Enzyme Data)

| Compound | hiNOS* IC50 [μM] | hecNOS* | hncNOS* |
|---|---|---|---|
| Example 1 | 154 | 1474 | 907 |

*hiNOS refers to recombinant human inducible NOS
hecNOS refers to recombinant human endothelial constitutive NOS
hncNOS refers to recombinant human neuronal constitutive NOS

TABLE III

Low Dose LPS*

| Compound | in vivo 0.1 | Effective Dose 1 | (p.o., mg/kg/day) 10 |
|---|---|---|---|
| Example 1 | 0% inh. | 54% inh. | 97% inh. |

*Low Dose LPS refers to the in vivo low-endotoxin assay carried out on rats as described above.

From the foregoing description, one skilled in the art can easily ascertain the essential characteristics of this invention, and without departing from the spirit and scope thereof, can make various changes and modifications of the invention to adapt it to various usage's and conditions.

What is claimed is:

1. A compound having the formula;

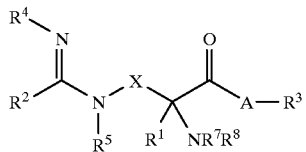

and pharmaceutically acceptable salts, wherein:

A is selected from O or S and may be taken together with $R^4$ to form a heterocyclic ring; or A is N when $R^3$ and $R^7$ are taken together to form a heterocyclic ring; or $R^5$ and A—$R^3$ are taken together to form a covalent bond; or A is N—$R^3$ provided $R^3$ is not a heterocyclic radical;

$R^1$ is not present or is selected from the group consisting of hydrogen, hydroxyalkyls, alkoxyalkyls, lower alkyls and haloalkyls;

$R^2$ is selected from the group consisting of straight and branched lower alkyls, lower alkenyls, and lower alkynyls, cycloalkyls, cycloalkenyls, haloalkyls;

$R^3$ is selected from the group consisting of aryl, heteroaryl, alkylaryl, alkylheteroaryl, all optionally substituted by one or more of halogen, nitrile, carboxy, carboxyalkyl, carboxyalkylaryl; or $R^3$ is selected from the group consisting of H, alkyl, alkenyl, $CH_2OC(=O)YR^6$, alkylhydroxy, alkylpolyhydroxy, alkyl(poly)oxyacyl, alkylcarboxy, optionally substituted by one or more of alkyl, hydroxy, amino, carboxy, carboxyalkyl, alkylcarbonyl;

$R^4$ is selected from H, OH, SH, $OR^6$, $SR^6$, $OC(=O)R^6$, $SC(=O)R^6$, $CH_2OC(=O)YR^6$, $OC(=O)YR^6$, $SC(=O)YR^6$;

Y is independently selected from O, S, $CH_2$, $CHR^6$, $C(R^6)_2$, NH, $NR^6$;

$R^5$ is selected from H, OH, SH, $OR^6$, $SR^6$, $OC(=O)R^6$, $SC(=O)R^6$, $CH_2OC(=O)YR^6$, $OC(=O)YR^6$, $SC(=O)YR^6$;

provided that $R^4$ and $R^5$ are not simultaneously hydrogen or $CH_2OC(=O)YR^6$.

$R^6$ is selected from hydrogen, alkyl, alkenyl, alkynyl, cycloalkyl, heterocyclic, aryl, heteroaryl all optionally substituted by one or more alkyl, alkoxy, hydroxy, halogen, trifluoromethyl, nitro, cyano, or amino groups;

$R^7$ is selected from H, $S(O)R^9$, $SO_2R^9$, $CH_2OC(O)$—$R^9$, $C(O)$—$R^9$ where $C(O)$—$R^9$ can represent natural and synthetic amino acids or $R^9$ can be defined as below, or $R^7$ and $R^3$ taken together comprise a 5- or 6- membered heterocyclic ring containing two or more heteroatoms, optionally substituted with alkyl and/or oxygen functions including carbonyl, or taken together comprise a metal complex containing a divalent cation, or a boron complex;

$R^8$ is selected from H, acyl;

$R^9$ is selected from substituted dihydropyridyl, alkyl, thioalkoxy, alkoxy, amino, cycloalkoxy, optionally substituted with one or more of amino, alkyl, alkylaryl, heteroaryl, alkylheteroaryl, alkylmercaptoalkyl, which may optionally be substituted with one or more of hydroxy, amino, guanidino, iminoalkyl;

X is selected from the group consisting of lower alkylenes, lower alkenylenes and lower alkynylenes and which may optionally be substituted by one or more alkyl, alkoxy, hydroxy, halogen, trifluoromethyl, nitro, cyano, or amino groups; or X is selected from the group consisting of the formula —$(CH_2)_kQ(CH_2)_t$— where k is 1, 2 or 3, t is 1, 2 or 3 and Q is O, Se, $SiE_2$ where E is lower alkyl, aryl, $S(O)_g$ where g is 0, 1 or 2, or NR where R is H or lower alkyl which may be optionally substituted with lower alkyl, lower alkoxy, hydroxy, halogen, trifluoromethyl, nitro, cyano, amino; or X is selected from the group consisting of the formula —$(CH_2)_mT(CH_2)_n$— where m is 0, 1 or 2, n is 0, 1 or 2, T is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

2. A compound having the formula;

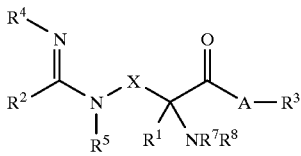

and pharmaceutically acceptable salts, wherein:

A is selected from O or S and may be taken together with $R^4$ to form a heterocyclic ring; or A is N when $R^3$ and $R^7$ are taken together to form a heterocyclic ring; or $R^5$ and A—$R^3$ are taken together to form a covalent bond; or A is N—$R^3$ provided $R^3$ is not a heterocyclic radical;

$R^1$ is selected from the group consisting of hydrogen, hydroxyalkyls of from 1 to 4 carbon atoms, alkoxyalkyls of from 1 to 4 carbon atoms in each position, lower alkyls of from 1 to 8 carbon atoms and haloalkyls of from 1 to 4 carbon atoms;

$R^2$ is selected from the group consisting of straight and branched lower alkyls of from 1 to 4 carbon atoms, lower alkenyls and lower alkynyls of from 2 to 4 carbon atoms, cycloalkyls of from 1 to 4 carbon atoms, cycloalkenyls of from 3 to 8 carbon atoms, and haloalkyls of from 1 to 4 carbon atoms;

$R^3$ is selected from the group consisting of aryl, heteroaryl, alkylaryl, alkylheteroaryl, all optionally substituted by one or more of halogen, nitrile, carboxy, carboxyalkyl, carboxyalkylaryl; or $R^3$ is also selected from the group consisting of H, alkyl of from 1 to 4 carbon atoms, alkenyl of from 2 to 4 carbon atoms, $CH_2OC(=O)YR^6$, alkylhydroxy, alkylpolyhydroxy, alkyl(poly)oxyacyl, alkylcarboxy, optionally substituted by one or more of alkyl of from 1 to 4 carbon atoms, hydroxy, amino, carboxy, carboxyalkyl, alkylcarbonyl;

$R^4$ is selected from H, OH, SH, $OR^6$, $SR^6$, $OC(=O)R^6$, $SC(=O)R^6$, $CH_2OC(=O)YR^6$, $OC(=O)YR^6$, $SC(=O)YR^6$;

Y is independently selected from O, S, $CH_2$, $CHR^6$, $C(R^6)_2$, NH, $NR^6$;

$R^5$ is selected from H, OH, SH, $OR^6$, $SR^6$, $OC(=O)R^6$, $SC(=O)R^6$, $CH_2OC(=O)YR^6$, $OC(=O)YR^6$, $SC(=O)YR^6$;

provided that $R^4$ and $R^5$ are not simultaneously hydrogen or $CH_2OC(=O)YR^6$;

$R^6$ is selected from hydrogen, alkyl of from 1 to 4 carbon atoms, alkenyl and alkynyl of from 2 to 4 carbon atoms, cycloalkyl of from 3 to 8 carbon atoms, heterocyclic of from 5 to 8 members, aryl, heteroaryl all optionally substituted by one or more alkyl of from 1 to 4 carbon atoms, alkoxy, hydroxy, halogen, trifluoromethyl, nitro, cyano, or amino groups;

$R^7$ is selected from H, $S(O)R^9$, $SO_2R^9$, $CH_2OC(O)$—$R^9$, $C(O)$—$R^9$ where $C(O)$—$R^9$ can represent natural and synthetic amino acids or $R^9$ can be defined as below, or $R^7$ and $R^3$ taken together comprise a 5- or 6- membered heterocyclic ring containing two or more heteroatoms, optionally substituted with alkyl of from 1 to 4 carbon atoms and/or oxygen functions including carbonyl, or taken together comprise a metal complex containing a divalent cation, or a boron complex;

$R^8$ is selected from H, acyl;

$R^9$ is selected from substituted dihydropyridyl, alkyl of from 1 to 4 carbon atoms, thioalkoxy, alkoxy, amino, cycloalkoxy, optionally substituted with one or more of amino, alkyl of from 2 to 4 carbon atoms, alkylaryl, heteroaryl, alkylheteroaryl, alkylmercaptoalkyl, which may optionally be substituted with one or more of hydroxy, amino, guanidino, iminoalkyl;

X is selected from the group consisting of alkylenes, alkenylenes and alkynylenes having 2 to 6 carbon atoms and which may optionally be substituted by one or more alkyl groups; or X is selected from the group consisting of the formula —$(CH_2)_kQ(CH_2)_t$— where k is 1, 2 or 3, t is 1, 2 or 3 and Q is O, Se, $SiE_2$ where E is lower alkyl, aryl, $S(O)_g$ where g is 0, 1 or 2, or NR where R is H or lower alkyl which may be optionally substituted with lower alkyl, lower alkoxy, hydroxy, halogen, trifluoromethyl, nitro, cyano, amino; or X is selected from the group consisting of the formula —$(CH_2)_mT(CH_2)_n$— where m is 0, 1 or 2, n is 0, 1 or 2, T is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

3. The compound as recited in claim 2 wherein

A is selected from O or S and may be taken together with $R^4$ to form a heterocyclic ring; or A is N when $R^3$ and $R^7$ are taken together to form a heterocyclic ring; or $R^5$ and A—$R^3$ are taken together to form a covalent bond; or A is N—$R^3$ provided $R^3$ is not a heterocyclic radical;

$R^1$ is selected from the group consisting of hydrogen, hydroxyalkyls of from 1 to 4 carbon atoms, alkoxyalkyls of from 1 to 4 carbon atoms in each position, lower alkyls of from 1 to 8 carbon atoms and haloalkyls of from 1 to 4 carbon atoms;

$R^2$ is selected from the group consisting of straight and branched lower alkyls of from 1 to 4 carbon atoms, lower alkenyls and lower alkynyls of from 2 to 4 carbon atoms, cycloalkyls of from 1 to 4 carbon atoms, cycloalkenyls of from 3 to 8 carbon atoms, and haloalkyls of from 1 to 4 carbon atoms;

$R^3$ is selected from the group consisting of aryl, heteroaryl, alkylaryl, alkylheteroaryl, all optionally substituted by one or more of halogen, nitrile, carboxy, carboxyalkyl, carboxyalkylaryl; or

73

R³ is also selected from the group consisting of H, alkyl of from 1 to 4 carbon atoms, alkenyl of from 2 to 4 carbon atoms, $CH_2OC(=O)YR^6$, alkylhydroxy, alkylpolyhydroxy, alkyl(poly)oxyacyl, alkylcarboxy;

R⁴ is selected from H, OH, SH, OR⁶, SR⁶, OC(=O)R⁶, SC(=O)R⁶, $CH_2OC(=O)YR^6$;

Y is independently selected from O, S, $CH_2$, CHR⁶, C(R⁶)₂, NH, NR⁶;

R⁵ is selected from H, OH, SH, OR⁶, SR⁶, OC(=O)R⁶, SC(=O)R⁶, $CH_2OC(=O)YR^6$;

provided that R⁴ and R⁵ are not simultaneously hydrogen;

R⁶ is selected from hydrogen, alkyl of from 1 to 4 carbon atoms, alkenyl and alkynyl of from 2 to 4 carbon atoms, cycloalkyl of from 3 to 8 carbon atoms, heterocyclic of from 5 to 8 members, aryl, heteroaryl all optionally substituted by one or more alkyl of from 1 to 4 carbon atoms or hydroxy groups;

R⁷ is selected from H, S(O)R⁹, SO₂R⁹, $CH_2OC(O)$—R⁹, C(O)—R⁹ where C(O)—R⁹ can represent natural and synthetic amino acids or R⁹ can be defined as below, or R⁷ and R³ taken together comprise a 5- or 6- membered heterocyclic ring containing two or more heteroatoms;

R⁸ is selected from H, acyl;

R⁹ is selected from substituted dihydropyridyl, alkyl of from 1 to 4 carbon atoms, thioalkoxy, alkoxy, amino, cycloalkoxy;

X is selected from the group consisting of alkylenes, alkenylenes and alkynylenes having 2 to 6 carbon atoms and which may optionally be substituted by one or more alkyl groups; or X is selected from the group consisting of the formula —(CH₂)$_k$Q(CH₂)$_t$— where k is 2 or 3, t is 1 or 2 and Q is O, Se, SiE₂ where E is lower alkyl, aryl, S(O)$_g$ where g is 0, 1 or 2, or NR where R is H or lower alkyl which may be optionally substituted with lower alkyl; or X is selected from the group consisting of the formula —(CH₂)$_m$T(CH₂)$_n$— where m is 0, 1 or 2, n is 0, 1 or 2, T is a 3 to 6 membered carbocyclic or heterocyclic ring, aromatic ring or heteroaromatic ring which may optionally be substituted by one or more substituents selected from the group consisting of lower alkyl, lower alkoxy, hydroxy halogen, nitro, cyano, trifluoroalkyl and amino.

4. The compound as recited in claim 3 wherein

A is selected from O and may be taken together with R⁴ to form a heterocyclic ring; or A is N when R⁵ and A—R³ are taken together to form a covalent bond;

A is N—R³ where the R³ radicals are selected from hydrogen, alkyl of from 1 to 4 carbon atoms or aryl;

R¹ is selected from the group consisting of hydrogen, hydroxyalkyls of from 1 to 4 carbon atoms and lower alkyls of from 1 to 8 carbon atoms;

R² is selected from the group consisting of straight and branched lower alkyls of from 1 to 4 carbon atoms and haloalkyls of from 1 to 4 carbon atoms;

R³ is selected from the group consisting of aryl, heteroaryl, alkylaryl, alkylheteroaryl, all optionally substituted by one or more of halogen, nitrile, carboxy, carboxyalkyl, carboxyalkylaryl; or R³ is also selected from the group consisting of H, alkyl of from 1 to 4 carbon atoms and alkenyl of from 2 to 4 carbon atoms;

74

R⁴ is selected from H, OH, SH, OR⁶, SR⁶;

R⁵ is selected from H, OH, SH, OR⁶, SR⁶;

provided that R⁴ and R⁵ are not simultaneously hydrogen;

R⁶ is selected from hydrogen, alkyl of from 1 to 4 carbon atoms, alkenyl and alkynyl of from 2 to 4 carbon atoms and cycloalkyl of from 3 to 8 carbon atoms;

R⁷ is selected from H and where C(O)—R⁹ can represent natural and synthetic amino acids;

R⁸ is selected from H and acyl;

X is selected from the group consisting of alkylenes, alkenylenes and alkynylenes having 2 to 6 carbon atoms and which may optionally be substituted by one or more alkyl groups; or X is selected from the group consisting of the formula —(CH₂)$_k$Q(CH₂)$_t$— where k is 2 or 3, t is 1 or 2 and Q is O, S(O)$_g$ where g is 0, 1 or 2, or NR where R is H or lower alkyl or X is selected from the group consisting of the formula —(CH₂)$_m$T(CH₂)$_n$— where m is 0, 1 or 2, n is 0, 1 or 2, T is a 3 to 6 membered carbocyclic or heterocyclic ring, aromatic ring or heteroaromatic ring.

5. The compound as recited in claim 4 wherein

A is O;

R¹ is hydrogen;

R² is methyl;

R³ is selected from the group consisting of hydrogen, and lower alkyls of 1 to about 4 carbon atoms;

R⁴ is hydroxy;

R⁵ is hydrogen or hydroxy;

R⁷ is hydrogen;

R⁸ is hydrogen;

X is an alkylene having 3 to 5 carbon atoms.

6. The pharmaceutical composition as recited in claim 3 wherein said compound is selected from the group consisting of;

N6-[1-(hydroxyimino)ethyl]-L-lysine, dihydrochloride 2-amino-5-[[1-(hydroxyimino)ethyl]amino]-2-methylpentanoic acid, dihydrochloride N6-[1-(hydroxyimino)ethyl]-2-methyl-L-lysine, dihydrochloride 2-[[2-[[1-(hydroxyimino)ethyl]amino]ethylseleno]methyl]-L-alanine, dihydrochloride N6-[1-(hydroxyimino)ethyl]-2-(hydroxymethyl)-L-lysine, dihydrochloride N6-[1-(hydroxyimino)-2,2,2-trifluoroethyl]-L-lysine, dihydrochloride N6-[1-(hydroxyimino)ethyl]-L-lysine, ethyl ester, dihydrochloride N6-[1-(hydroxyimino)ethyl]-L-lysine, 2,3-dihydroxypropyl ester, dihydrochloride N6-[1-(hydroxyimino)ethyl]-L-lysine, 2-hydroxy-1-(hydroxymethyl)ethyl ester, dihydrochloride N6-[1-(hydroxyimino)ethyl]-L-lysine, 2-(diethylamino)-2-oxoethyl ester, dihydrochloride S-ethyl 2S-amino-6-[[1(hydroxyimino)ethyl]amino] hexanethioate, dihydrochloride N2-[(acetyloxy)methyl]-N6-[1-(hydroxyimino)ethyl]-L-lysine, dihydrochloride N6-[1-(hydroxyimino)ethyl]-N2-[[[(methylamino) carbonyl]oxy]methyl]-L-lysine, dihydrochloride N6-[1-(hydroxyimino)ethyl]-N2-[[(methoxycarbonyl)oxy] methyl]-L-lysine, dihydrochloride N6-[1-(hydroxyimino)ethyl]-N2-[[[(methylthio)carbonyl] oxy]methyl]-L-lysine, dihydrochloride N6-[1-(hydroxyimino)ethyl]-N2-[[(phenylcarbonyl)oxy]methyl]-L-lysine, dihydrochloride
N2-acetyl-N2-[(acetyloxy)methyl]-N6-[1-(hydroxyimino)ethyl]-L-lysine, hydrochloride
N6-[1-(hydroxyimino)ethyl]-N2-[(methylthio)carbonyl]-L-lysine, hydrochloride
N2-[(1,1-dimethylethoxy)carbonyl]-N6-[1-(hydroxyimino)ethyl]-L-lysine, hydrochloride
N6-[1-(hydroxyimino)ethyl]-N2-[(methylamino)carbonyl]-L-lysine, hydrochloride
N6-[1-(hydroxyimino)ethyl]-N2-[N6-[1-(hydroxyimino)ethyl]-L-lysyl]-L-lysine, ethyl ester, trihydrochloride
N6-[1-(hydroxyimino)ethyl]-N2-[N6-[1-(hydroxyimino)ethyl]-L-lysyl]-L-lysine, trihydrochloride
N6-[1-(hydroxyimino)ethyl]-N2-[N6-(1-iminoethyl)-L-lysyl]-L-lysine, ethyl ester, trihydrochloride
N6-[1-(hydroxyimino)ethyl]-N2-[N6-(1-iminoethyl)-L-lysyl]-L-lysine, trihydrochloride
N2-(N-acetyl-L-methionyl)-N6-[1-(hydroxyimino)ethyl]-L-lysine, ethyl ester, hydrochloride
N2-(N-acetylmethionyl)-N6-[1-(hydroxyimino)ethyl]-L-lysine, hydrochloride
N2-(L-alanyl)-N6-[1-(hydroxyimino)ethyl]-L-lysine, dihydrochloride
N6-[1-[[(methoxycarbonyl)oxy]imino]ethyl]-L-lysine, dihydrochloride
N6-[1-[[[(methylamino)carbonyl]oxy]imino]ethyl]-L-lysine, dihydrochloride
N6-[1-[[[(methylthio)carbonyl]oxy]imino]ethyl]-L-lysine, dihydrochloride
N6-[1-[(acetyloxy)imino]ethyl]-L-lysine, dihydrochloride
N6-[1-[[(phenylcarbonyl)oxy]imino]ethyl]-L-lysine, dihydrochloride
N6-[1-[(methoxyimino)ethyl]-L-lysine, dihydrochloride
N6-[1-[(phenoxyimino)ethyl]-L-lysine, dihydrochloride
N6-hydroxy-N6-[1-(hydroxyimino)ethyl]-L-lysine, dihydrochloride
N6-[1-(hydroxyimino)ethyl]-N6-[[(methoxycarbonyl)oxy]methyl]-L-lysine, dihydrochloride
N6-[1-(hydroxyimino)ethyl]-N6-[[[(methylamino)carbonyl]oxy]methyl]-L-lysine, dihydrochloride
N6-[1-(hydroxyimino)ethyl]-N6-[[[(methylthio)carbonyl]oxy]methyl]-L-lysine, dihydrochloride
N6-[1-(hydroxyimino)ethyl]-N6-[[(phenylcarbonyl)oxy]methyl]-L-lysine, dihydrochloride
N6-(acetyloxy)-N6-(1-iminoethyl)-L-lysine, dihydrochloride
N6-[1-[(phenylthio)imino]ethyl]-L-lysine, dihydrochloride
N6-(1-iminoethyl)-N6-(phenylmethoxy)-L-lysine, dihydrochloride
N6-hydroxy-N6-(1-iminoethyl)-L-lysine, dihydrochloride
N6-acetyloxy-N6-[1-[(acetyloxy)imino]ethyl]-L-lysine, dihydrochloride
N6-[1-[[(methoxycarbonyl)oxy]imino]ethyl]-N6-[(methoxycarbonyl)oxy]-L-lysine, dihydrochloride
N6-[1-[[[(methylamino)carbonyl]oxy]imino]ethyl]-N6-[[(methylamino)carbonyl]oxy]-L-lysine, dihydrochloride
N6-[1-[[[(methylthio)carbonyl]oxy]imino]ethyl]-N6-[[(methylthio)carbonyl]oxy]-L-lysine, dihydrochloride
N6-[1-[[(phenylcarbonyl)oxy]imino]ethyl]-N6-[(phenylcarbonyl)oxy]-L-lysine, dihydrochloride
N6-[1-(phenoxyimino)ethyl]-N6-phenoxy-L-lysine, dihydrochloride
N6-[1-(methoxyimino)ethyl]-N6-(phenylmethoxy)-L-lysine, dihydrochloride
N6-[1-[[(acetyloxy)methyl]imino]ethyl]-N6-hydroxy-L-lysine, dihydrochloride
N6-hydroxy-N6-[1-[[[(methoxycarbonyl)oxy]methyl]imino]ethyl]-L-lysine, dihydrochloride
N6-hydroxy-N6-[1-[[[[(methylamino)carbonyl]oxy]methyl]imino]ethyl]-L-lysine, dihydrochloride
N6-hydroxy-N6-[1-[[[[(methylthio)carbonyl]oxy]methyl]imino]ethyl]-L-lysine, dihydrochloride
N6-hydroxy-N6-[1-[[[(phenylcarbonyl)oxy]methyl]imino]ethyl]-L-lysine, dihydrochloride
N6-[(acetyloxy)methyl]-N6-[1-(hydroxyimino)ethyl]-L-lysine, dihydrochloride
N6-(1-iminoethyl)-N6-[(methoxycarbonyl)oxy]-L-lysine, dihydrochloride
N6-(1-iminoethyl)-N6-[[(methylamino)carbonyl]oxy]-L-lysine, dihydrochloride
N6-(1-iminoethyl)-N6-[[(methylthio)carbonyl]oxy]-L-lysine, dihydrochloride
N6-(1-iminoethyl)-N6-[(phenylcarbonyl)oxy]-L-lysine, dihydrochloride
N6-(1-iminoethyl)-N6-phenoxy-L-lysine, dihydrochloride
N6-[1-[(methylthio)imino]ethyl]-L-lysine, dihydrochloride
N6-(1-iminoethyl)-N6-(methylthio)-L-lysine, dihydrochloride
N6-(1-iminoethyl)-N6-(phenylthio)-L-lysine, dihydrochloride
N6-[1-[(phenylthio)imino]ethyl]-L-lysine, dihydrochloride
5-[4-[[1-(hydroxyimino)ethyl]amino]butyl]imidazolidine-2,4-dione, dihydrochloride
N-[N6-[1-(hydroxyimino)ethyl]-L-lysyl]-L-alanine, dihydrochloride
2S-amino-6-[[1-(hydroxyimino)ethyl]amino]-4-hexenoic acid, dihydrochloride
N-[2S-amino-2-[3-[[[1-(hydroxyimino)ethyl]amino]methyl]cyclopentyl]acetyl]-L-alanine, dihydrochloride
N-[2S-amino-2-[3-[[[1-(hydroxyimino)ethyl]amino]methyl]isoxazol-5-yl]acetyl]-L-alanine, dihydrochloride
N2-(4-amino-1-oxobutyl)-N6-[1-(hydroxyimino)ethyl]-L-lysine, ethyl ester, dihydrochloride
N2-[[(2-aminoethyl)amino]carbonyl]-N6-[1-(hydroxyimino)ethyl]-L-lysine, ethyl ester, dihydrochloride
N2-[(2-aminoethoxy)carbonyl]-N6-[1-(hydroxyimino)ethyl]-L-lysine, ethyl ester, dihydrochloride
9S-amino-5,6,7,8,9,10-hexahydro-3-methyl-4H-1,2,4-oxadiazecin-10-one, dihydrochloride
3S-aminohexahydro-1-[1-(hydroxyimino)ethyl]-2H-azepin-2-one, dihydrochloride.

7. A method of inhibiting nitric oxide synthesis in a subject in need of such inhibition by administering a therapeutically effective amount of a compound of claims 1, 2, 3, 4, 5, or 6.

8. A method of selectively inhibiting nitric oxide synthesis produced by inducible NO synthase over nitric oxide produced by the constitutive forms of NO synthase in a subject in need of such selective inhibition by administering a therapeutically effective amount of a compound of claims 1, 2, 3, 4, 5, or 6.

9. A method of lowering nitric oxide levels in a subject in need of such by administering a therapeutically effective amount of a compound of claims 1, 2, 3, 4, 5, or 6.

10. A pharmaceutical composition comprising a compound of claims 1, 2, 3, 4, 5, or 6 together with one or more pharmaceutically acceptable carriers.

* * * * *